(12) United States Patent
Yamauchi et al.

(10) Patent No.: US 6,736,813 B2
(45) Date of Patent: May 18, 2004

(54) HIGH-FREQUENCY TREATMENT TOOL

(75) Inventors: Koji Yamauchi, Koganei (JP); Naomi Sekino, Hachioji (JP); Koji Iida, Sagamihara (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/884,920

(22) Filed: Jun. 20, 2001

(65) Prior Publication Data
US 2001/0037109 A1 Nov. 1, 2001

Related U.S. Application Data

(63) Continuation-in-part of application No. 09/234,161, filed on Jan. 21, 1999, now Pat. No. 6,273,887.

(30) Foreign Application Priority Data

| Jan. 23, 1998 | (JP) | 10-011199 |
| Aug. 27, 1998 | (JP) | 10-241561 |
| Sep. 2, 1998 | (JP) | 10-248625 |
| Sep. 2, 1998 | (JP) | 10-248673 |
| Oct. 16, 1998 | (JP) | 10-295372 |
| Jan. 21, 1999 | (JP) | 11-012914 |
| Jul. 5, 2000 | (JP) | 2000-203938 |
| Jan. 5, 2001 | (JP) | 2001-000703 |

(51) Int. Cl.[7] .............................................. A61B 18/14
(52) U.S. Cl. ............................ 606/48; 606/37; 606/39; 606/40; 606/51
(58) Field of Search ................ 606/45, 46, 48, 606/50–52, 39, 40, 37

(56) References Cited

U.S. PATENT DOCUMENTS

| 4,492,231 A | 1/1985 | Auth |
| 5,269,780 A | 12/1993 | Roos |
| 5,626,578 A * | 5/1997 | Tihon ................... 606/48 |
| 5,688,270 A | 11/1997 | Yates et al. |
| 5,702,390 A | 12/1997 | Austin et al. |
| 5,827,271 A * | 10/1998 | Buysse et al. ........... 606/40 |
| 5,853,412 A | 12/1998 | Mayenberger |
| 5,876,401 A * | 3/1999 | Schulze et al. .......... 606/51 |
| 5,891,142 A | 4/1999 | Eggers et al. |
| 6,024,744 A | 2/2000 | Kese et al. |
| 6,187,003 B1 | 2/2001 | Buysse et al. |
| 6,364,879 B1 * | 4/2002 | Chen et al. ............ 606/48 |
| H2037 H * | 7/2002 | Yates et al. ........... 606/51 |
| 6,451,018 B1 * | 9/2002 | Lands et al. ........... 606/50 |

FOREIGN PATENT DOCUMENTS

| DE | 40 32 471 C2 | 4/1992 |
| DE | 41 38 116 A1 | 6/1993 |
| EP | 0 598 348 A1 | 5/1994 |
| JP | 07-171163 | 7/1995 |
| JP | 08-317934 | 12/1996 |
| JP | 8-317936 | 12/1996 |
| JP | 10-199 | 1/1998 |
| JP | 11-137562 A | 5/1999 |
| JP | 11-155877 | 6/1999 |
| JP | 2000-70280 A | 3/2000 |

* cited by examiner

Primary Examiner—Lee Cohen
(74) Attorney, Agent, or Firm—Frishauf, Holtz, Goodman & Chick, P.C.

(57) ABSTRACT

The present invention provides a bipolar high-frequency treatment tool for coagulating and incising the vital tissue, comprising a pair of jaws provided at a distal end portion of an elongated member such that they can be closed and opened between a closed position and an open position, an operation unit having a handle provided at a proximal end portion of the elongated member, the operation unit closing and opening the jaws when the handle is operated, a first electrode portion provided at one of the jaws, and a second electrode portion provided at the other of the jaws. When vital tissue is gripped between the jaws, the effective electrode surface of the second electrode portion, which is to be brought into contact with the vital tissue, is smaller than that of the second electrode portion.

34 Claims, 26 Drawing Sheets

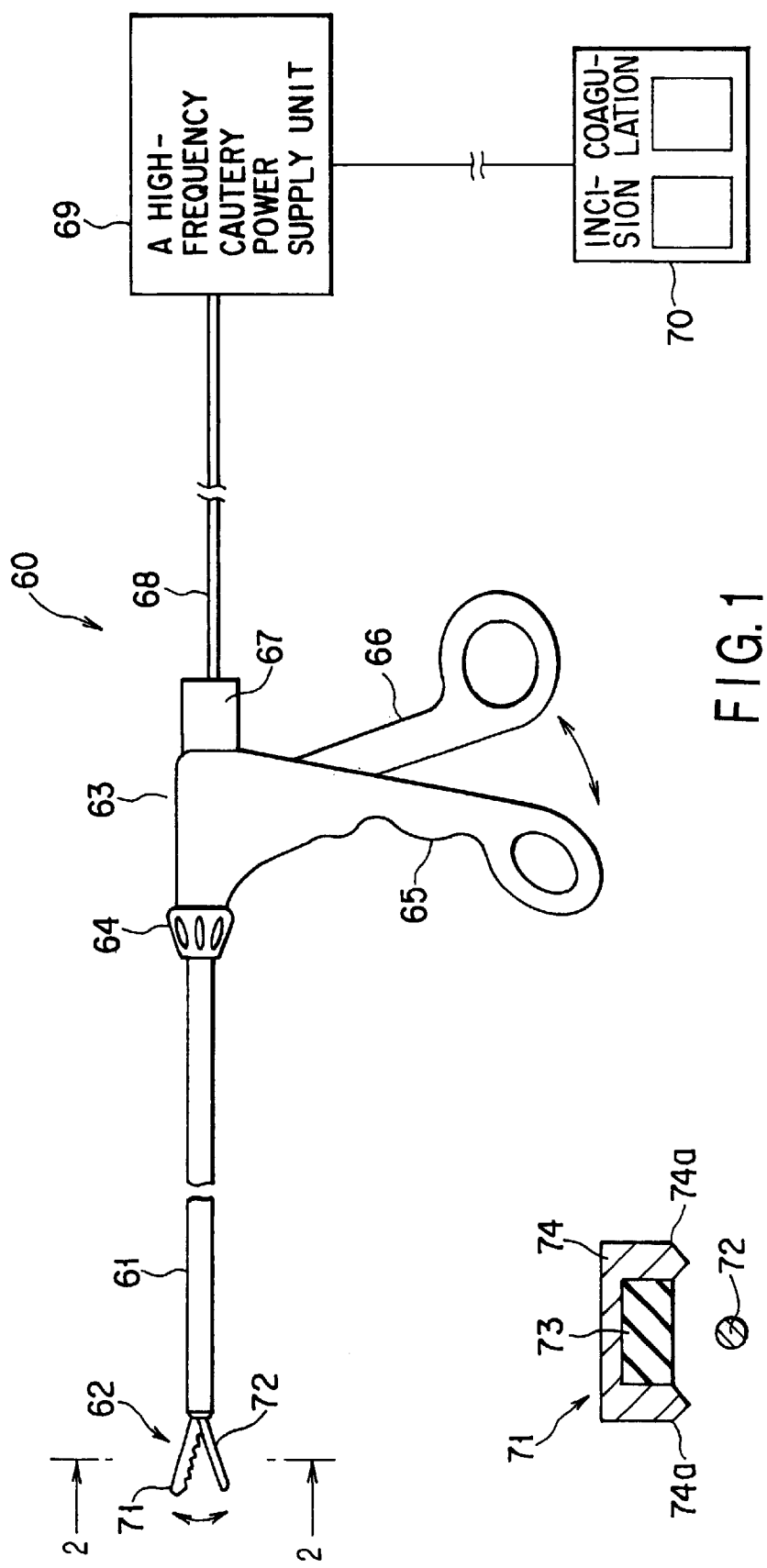

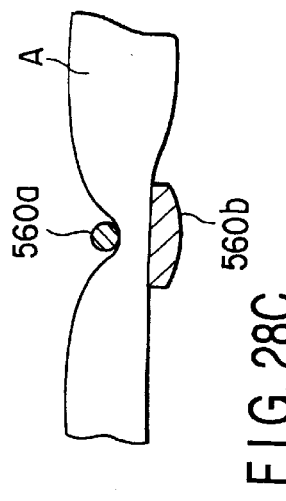
FIG. 28A
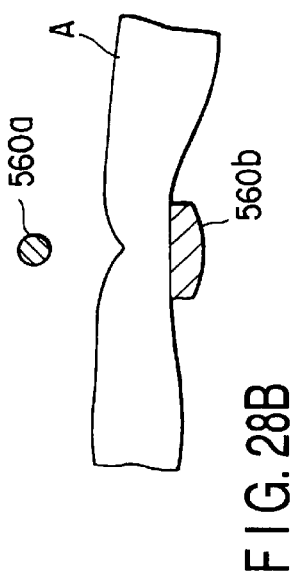
FIG. 28B
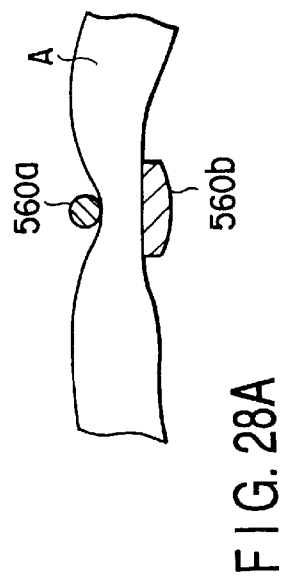
FIG. 28C
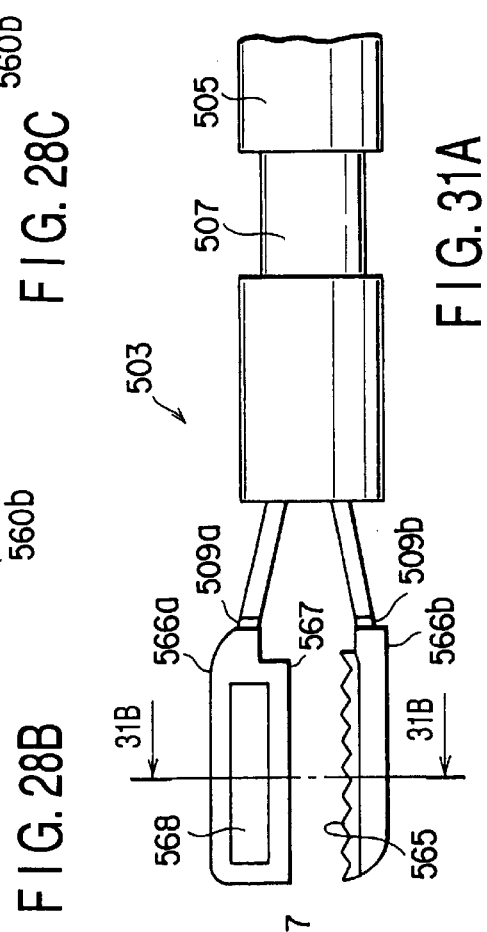
FIG. 31A
FIG. 31B  FIG. 31C
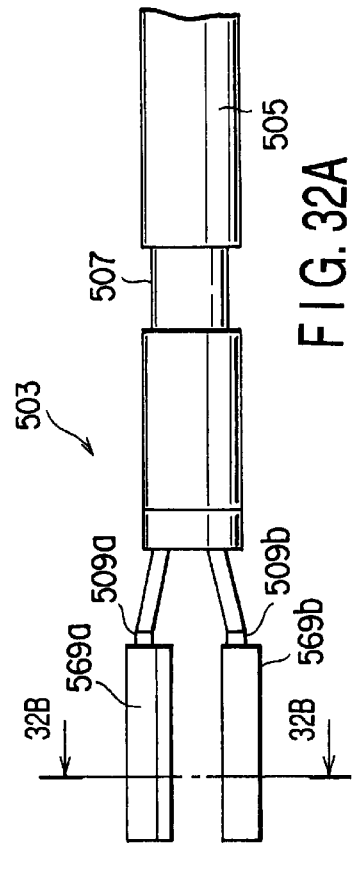
FIG. 32A
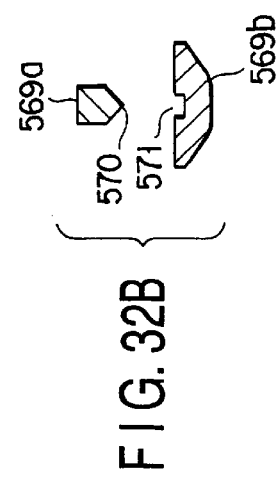
FIG. 32B

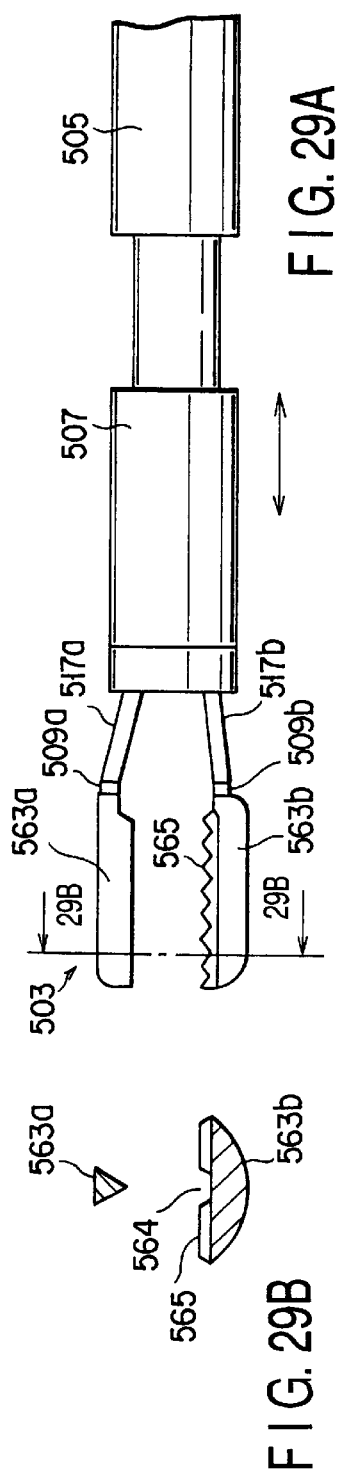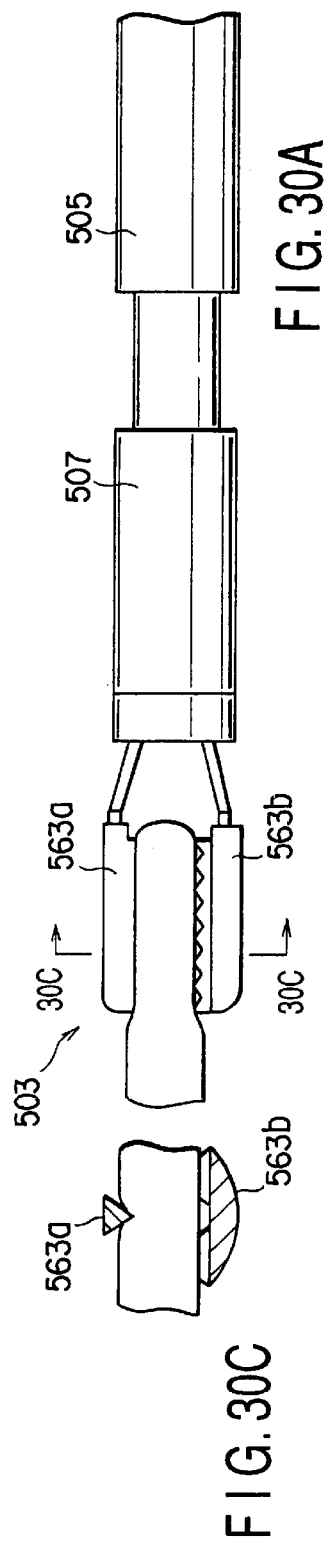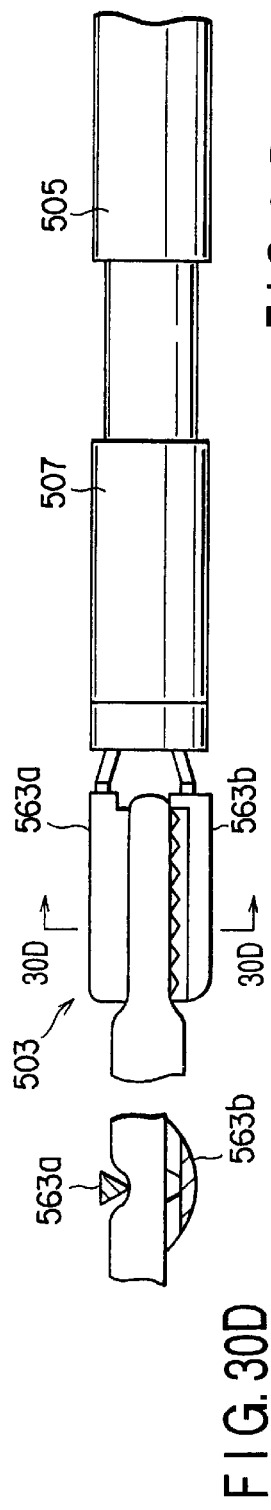

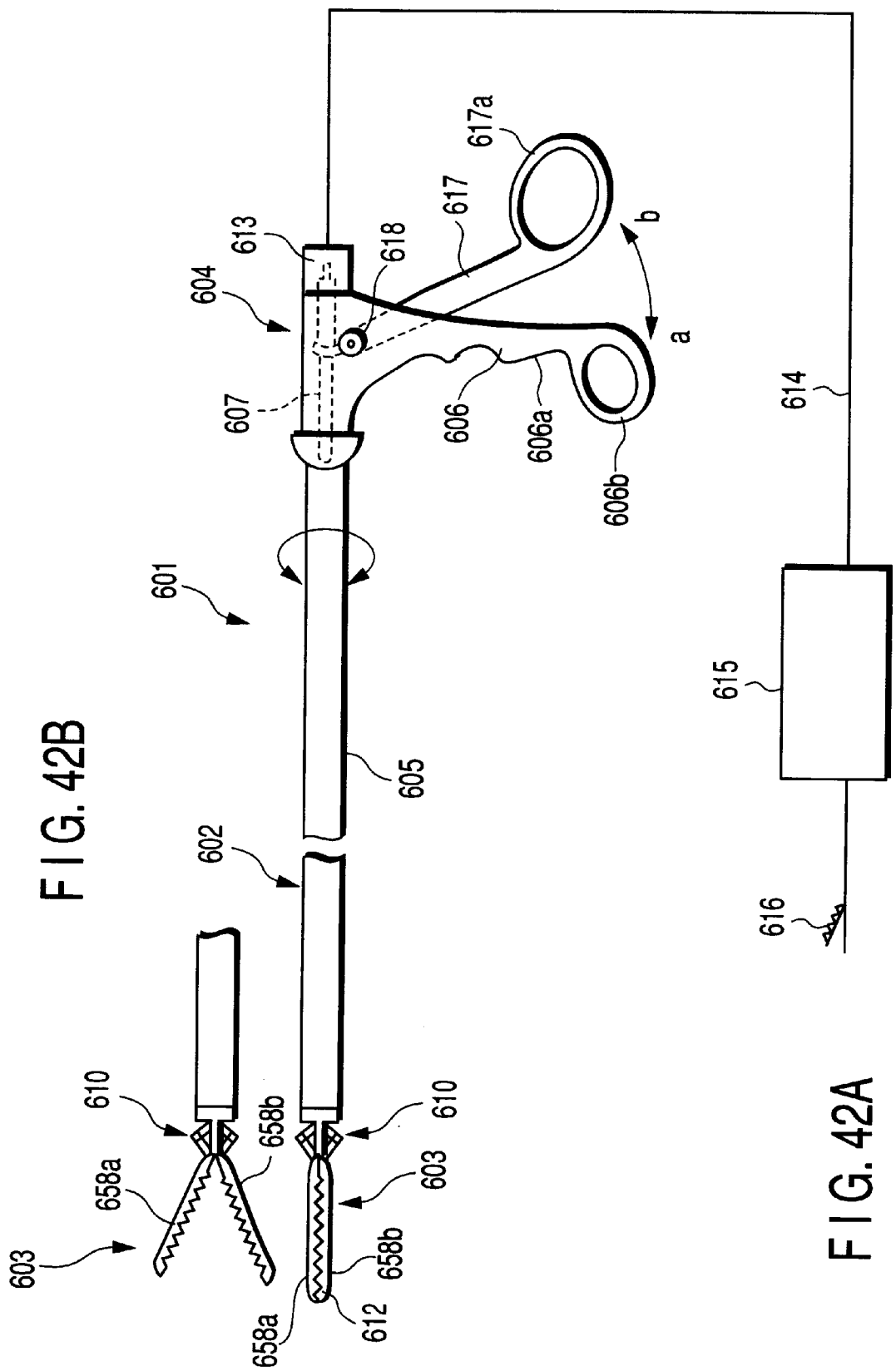

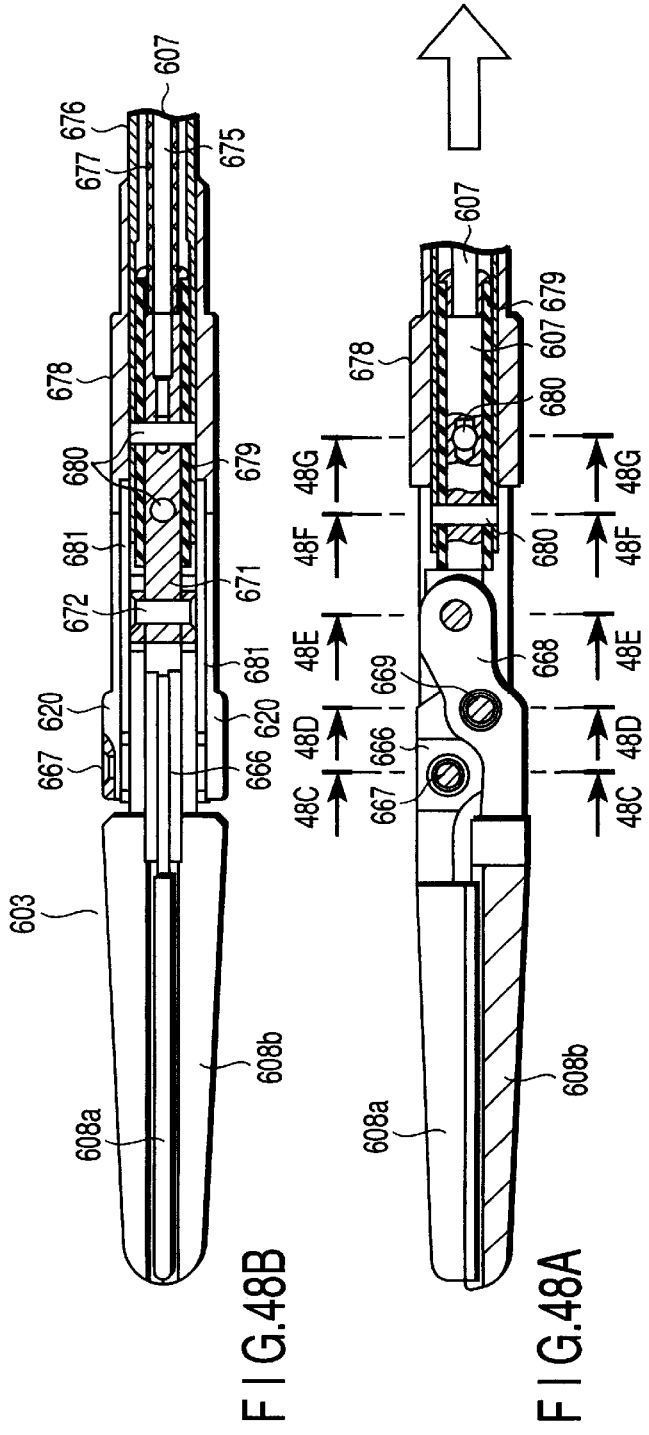
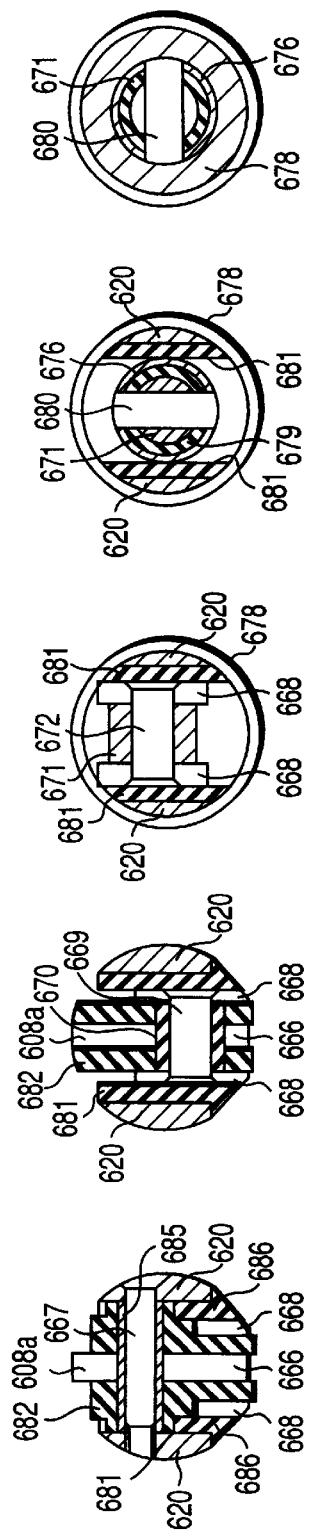

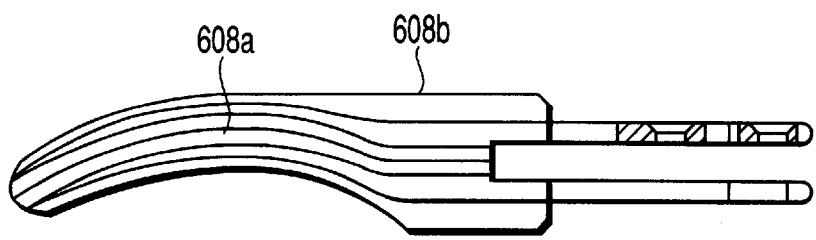
FIG. 52A
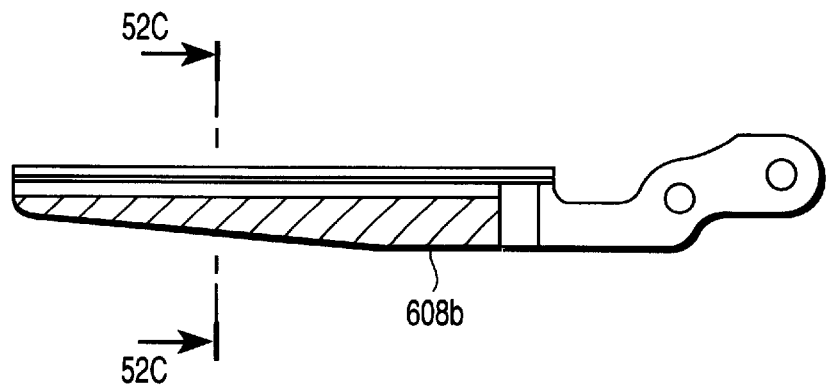
FIG. 52B
FIG. 52C
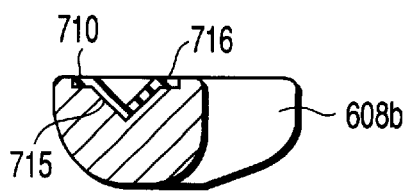
FIG. 52D
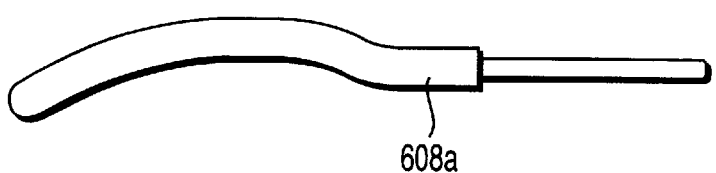
FIG. 52F
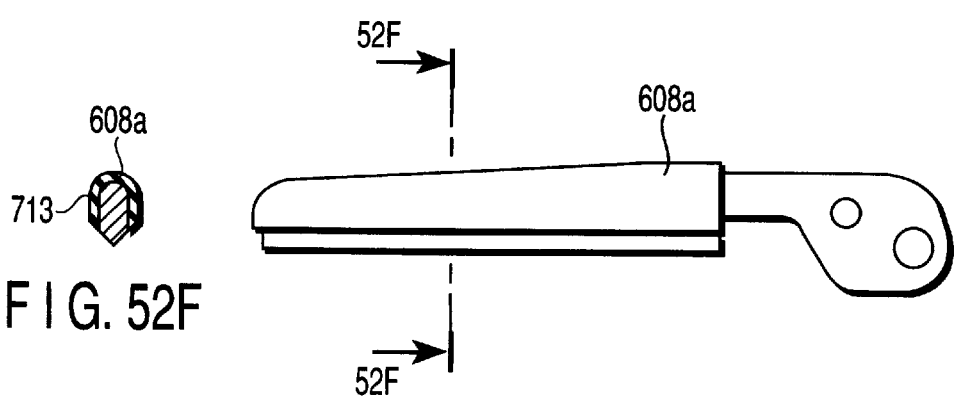
FIG. 52E

HIGH-FREQUENCY TREATMENT TOOL

CROSS-REFERENCE TO RELATED APPLICATIONS

This is a Continuation-in-Part application of U.S. patent application Ser. No. 09/234,161, filed Jan. 21, 1999, now U.S. Pat. No. 6,273,887, the entire contents of which are incorporated herein by reference.

This application is based upon and claims the benefit of priority from the prior Japanese Patent Applications No. 10-011199, filed Jan. 23, 1998; No. 10-241561, filed Aug. 27, 1998; No. 10-248625, filed Sep. 2, 1998; No. 10-248673, filed Sep. 2, 1998; No. 10-295372, filed Oct. 16, 1998; No. 11-012914, filed Jan. 21, 1999; No. 2000-203938, filed Jul. 5, 2000; and No. 2001-000703, filed Jan. 5, 2001, the entire contents of all of which are incorporated herein by reference.

BACKGROUND OF THE INVENTION

The present invention relates to a high-frequency treatment tool which can grip tissue in a body and coagulate/incise it.

A bipolar forceps is known as a high-frequency treatment tool capable of gripping, coagulating and incising vital tissue. In general, the bipolar forceps has jaws as a pair of gripping members for gripping vital tissue, and high-frequency current supply electrodes formed on the jaws. In this bipolar forceps, when vital tissue to be treated is gripped between the pair of jaws, and a high-frequency current is flowed across the electrodes of the jaws, the vital tissue between the jaws is coagulated or incised.

Bipolar forcipes of this type are disclosed in U.S. Pat. No. 6,024,744, EP 0598348 A1, DE 4032471 C2, and Jpn. Pat. Appln. KOKAI Publication No. 10-199.

The forceps disclosed in U.S. Pat. No. 6,024,744 is a bipolar forceps formed by combining standard surgical scissors with grasping forceps. In this bipolar forceps, a section for coagulating tissue using a high-frequency wave, and a section for mechanically incising tissue are formed in line on the jaws. Since thus, the section for coagulating tissue using high-frequency wave is separate from the section for mechanically incising tissue in the back-and-forth direction, it is necessary to shift vital tissue when mechanically incising the vital tissue after coagulating it using a high-frequency wave. Thus, the operation of the forceps is complicated when performing both coagulation and incision. Further, since the section for coagulating vital tissue using a high-frequency wave is situated at the proximal end side of the jaws, the incising section located at the distal end side of the jaws makes it difficult to coagulate target tissue accurately and delicately.

In a bipolar forceps disclosed in EP 0598348 A1, one of a pair of electrodes is formed of a wire. Using the wire electrode, the forceps incise vital tissue. To coagulate vital tissue, another tool is needed to perform the job.

In a bipolar forceps disclosed in DE 4032471 C2, three electrodes, which include a pair of rod-shaped coagulating electrodes and an incising wire electrode, are used to coagulate and incise vital tissue. Further, the power supply mode is changed between the coagulating electrodes and the incising electrode. Since, in this case, the single wire electrode is used as an incising electrode, and the other rod-shaped electrodes are used as coagulating electrodes, the area needed for the operation of the tool to perform a certain treatment is relatively large, which makes it difficult to perform delicate operations on vital tissue.

Moreover, in this case, three electrodes are necessary, and the power supply mode must be switched between that of coagulating vital tissue and that of incising it. This power switching operation is complicated, which makes it difficult to perform a quick treatment. In addition, the use of three electrodes and the power mode switching between the three electrodes make the electrode structure and power supply structure complicated.

Jpn. Pat. Appln. KOKAI Publication No. 10-199 discloses a technique for rotating, about its longitudinal axis, an electrode member having a coagulation electrode surface and an incision edge electrode, thereby changing the direction of the electrode surface to execute both coagulation and incision of vital tissue. In this technique, when switching the operation between coagulation of vital tissue and its incision, it is necessary to, for example, rotate the electrode member about its longitudinal axis so as to change its direction. Further, when incising coagulated tissue, it is necessary to release the gripped tissue and then to change the direction of the electrode member. Accordingly, the states of the movable jaws must be adjusted by the operation section each time the setting is changed. Thus, operation of the treatment tool is complicated, which makes it difficult to execute a quick treatment. Moreover, to enable the rotation of the electrode member about its longitudinal axis, the electrode support structure and the operation mechanism are necessarily complicated.

BRIEF SUMMARY OF THE INVENTION

It is the object of the present invention to provide a high-frequency treatment tool having an electrode structure capable of treating vital tissue delicately, and performing treating of vital tissue efficiently.

To attain the object, there is provided a bipolar high-frequency treatment tool for gripping vital tissue between two electrically insulated electrode portions, and supplying a high frequency current to the vital tissue gripped between the two electrode portions, thereby coagulating or incising the vital tissue, comprising:

an elongated member;

a pair of jaws provided at a distal end portion of the elongated member such that they can be closed and opened between a closed position and an open position;

an operation unit having a handle provided at a proximal end portion of the elongated member, the operation unit closing and opening the jaws when the handle is operated;

a first electrode portion provided at one of the jaws, and having a first effective electrode surface to be brought into contact with vital tissue when the vital tissue is gripped between the jaws;

a second electrode portion provided at the other of the jaws, opposed to the first electrode portion, and having a second effective electrode surface to be brought into contact with vital tissue when the vital tissue is gripped between the jaws, the second effective electrode surface being smaller than the first effective electrode surface; and a current supply unit for supplying a treatment high-frequency current to the first and second electrode portions, thereby supplying the treatment high-frequency current to the vital tissue when the jaws are closed to grip the vital tissue between the first and second electrode portions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a side view of a high-frequency treatment tool according to a 1st embodiment of the present invention;

FIG. 2 is a sectional view taken along line 2—2 in FIG. 1;

FIGS. 28A to 28C are sectional views showing a way of use of a high-frequency treatment tool according to a modification of the 17th embodiment;

FIG. 29A is a side view of the distal end side of a high-frequency treatment tool according to an 18th embodiment of the present invention;

FIG. 29B is a sectional view taken along line 29B—29B in FIG. 29A;

FIGS. 30A and 30B are side views showing a use form of the high-frequency treatment tool shown in FIG. 29A;

FIGS. 30C and 30D are sectional views taken along line 30C—30C in FIG. 30A and line 30D—30D in FIG. 30B, respectively;

FIG. 31A is a side view of the distal end side of a high-frequency treatment tool according to a 19th embodiment of the present invention;

FIG. 31B is a sectional view taken along line 31B—31B in FIG. 31A;

FIG. 31C is a front view of the distal end side of a high-frequency treatment tool according to a 19th embodiment of the present invention;

FIG. 32A is a side view of the distal end side of a high-frequency treatment tool according to a 20th embodiment of the present invention;

FIG. 32B is a sectional view taken along a line 32B—32B in FIG. 32A;

FIG. 42A is a view illustrating the overall arrangement of a high-frequency treatment tool according to a 23rd embodiment of the present invention;

FIG. 42B is a view useful in explaining a treatment portion of the high-frequency treatment tool of the 23rd embodiment in the open state;

FIG. 48A is a longitudinal sectional view illustrating a distal end portion of the high-frequency treatment tool shown in FIG. 47A;

FIG. 48B is another longitudinal sectional view illustrating the distal end portion of the high-frequency treatment tool shown in FIG. 47A;

FIG. 48C is a sectional view taken along line 48C—48C in FIG. 48A;

FIG. 48D is a sectional view taken along line 48D—48D in FIG. 48A;

FIG. 48E is a sectional view taken along line 48E—48E in FIG. 48A;

FIG. 48F is a sectional view taken along line 48F—48F in FIG. 48A;

FIG. 48G is a sectional view taken along line 48G—48G in FIG. 48A;

FIG. 52A is a view useful in explaining a modification of the treatment portion of the high-frequency treatment tool according to the 24th embodiment of the present invention;

FIG. 52B is a view useful in explaining another modification of the treatment portion of the high-frequency treatment tool according to the 24th embodiment of the present invention;

FIG. 52C is a view taken along line 52C—52C in FIG. 52B;

FIG. 52D is a view useful in explaining yet another modification of the treatment portion of the high-frequency treatment tool according to the 24th embodiment of the present invention;

FIG. 52E is a view useful in explaining a further modification of the treatment portion of the high-frequency treatment tool according to the 24th embodiment of the present invention;

FIG. 52F is a view taken along line 52F—52F in FIG. 52E; and

DETAILED DESCRIPTION OF THE INVENTION

Figure 3A:
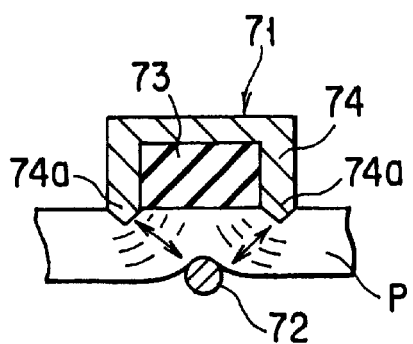
FIGS. 3A and 3B are sectional views showing a way of use of the high-frequency treatment tool shown in FIG. 1.

The embodiments of the present invention will be described with reference to the accompanying drawing.

FIGS. 1 to 3B show a 1st embodiment of the present invention. As shown in FIG. 1, a bipolar forceps 60 as a high-frequency treatment tool according to this embodiment comprises a sheath 61 as an insertion portion to be inserted into the body cavity of a patient, a treatment portion 62 attached to the distal end portion of the sheath 61 to grip vital tissue and coagulate or incise it, and an operation portion 63 coupled to the proximal end portion of the sheath 61. The sheath 61 is rotated by operating a rotary operation portion 64 on the operation portion 63 side.

The treatment portion 62 has a pair of jaws 71 and 72 which can be opened/closed. The operation portion 63 has a fixed handle 65 and a movable handle 66. The jaws 71 and 72 are opened/closed by pivoting the movable handle 66.

A conductive member serving as a path for supplying a high-frequency current is electrically connected to the jaws 71 and 72. This conductive member extends through the sheath 61 and is connected to a connector receptacle 67 of the operation portion 63. A cable 68 extending from a high-frequency cautery power supply unit 69 is connected to the connector receptacle 67. The high-frequency cautery power supply unit 69 has a foot switch 70 for turning on/off the power supply unit 69. The foot switch 70 has an incision switch portion and a coagulation switch portion.

As shown in FIG. 2 in detail, the first jaw 71 on one side of the treatment portion 62 comprises a main body portion 74 formed from a conductive material and having a U-shaped section. Serrate gripping portions 74a are formed on both sides of the main body portion 74. The gripping portions 74a constitute a first electrode portion.

In the main body portion 74, an insulating member 73 for gripping tissue together with the gripping portions 74a is fixed between the gripping portions 74a. This insulating member 73 is substantially arranged throughout the total length of the main body portion 74.

The second jaw 72 on the other side of the treatment portion 62 is formed as a rod consisting of a conductive material and having a circular section. The second jaw 72 constitutes a second electrode portion. The second jaw 72 is located to come into contact with only the insulating member 73 when the treatment portion 62 is closed.

When vital tissue is gripped between the pair of jaws 71 and 72, the effective electrode surface of the second electrode portion, which is in contact with the vital tissue, is smaller than that of the first electrode portion.

Figure 3B:
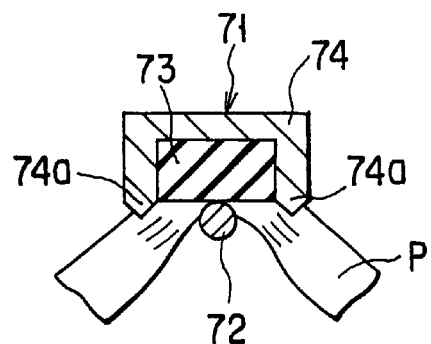

FIGS. 3A and 3B show steps of coagulating/incising tissue P using the bipolar forceps 60 having the above arrangement. FIG. 3A shows a state wherein the tissue P is sandwiched by the gripping portions 74a of the first jaw 71 and the second jaw 72. Even when the tissue P is membranous one, the jaws 71 and 72 to which a high-frequency current is supplied do not come into contact. This is because when the treatment portion 62 is completely closed, the second jaw 72 comes into contact with only the insulating member 73. While the tissue P is sandwiched by the gripping portions 74a of the first jaw 71 and the second jaw 72, a coagulation current is flowed across the jaws 72 and 72 to coagulate the tissue P.

Upon completing coagulation, the treatment portion 62 is more tightly closed to sandwich the tissue P by the gripping portions 74a of the first jaw 71, insulating member 73, and second jaw 72. At this time as well, the jaws 71 and 72 do not come into contact with each other. In this state, an incision current is flowed across the jaws 71 and 72 to incise the tissue P.

As described above, in the bipolar forceps 60 of this embodiment, when the treatment portion 62 is completely closed, the second jaw 72 comes into contact with only the insulating member 73 of the first jaw 71. That is, when tissue is gripped by the jaws 71 and 72, the electrode portions to which a high-frequency current is supplied do not come into contact with each other. Hence, no electrical short circuit occurs between the jaws 71 and 72, and even thin membranous tissue can be reliably coagulated or incised.

In the bipolar forceps 60 of this embodiment, when vital tissue is gripped between the pair of jaws 71 and 72, the effective electrode surface of the second electrode portion at the jaw 72 side, which actually touches the vital tissue, is smaller than that of the first electrode portion at the jaw 71 side. Accordingly, a current concentrates on the second electrode portion at the jaw 72 side, thereby enabling a local coagulation treatment and incision treatment. This forceps can also perform the coagulation treatment and the incision treatment continuously and efficiently, while gripping the vital tissue.

Further, the insulating member 73 is sandwiched by the gripping portions 74a of the first jaw 71, and the tissue is also gripped by this insulating member 73. Hence, the operator can reliably grip the tissue without missing it and coagulate/incise it (Especially, when the tissue is gripped by part of the jaws or the jaw has a rod shape, as in this embodiment, an insulating member commonly used as a gripping means and a short circuit prevention means is very effective). To the contrary, a high-frequency treatment tool disclosed in DE 4032471 C2 grips tissue by three rod electrodes. For this reason, the tissue is missed upon gripping and cannot be reliably gripped, and coagulation or incision cannot be reliably performed.

Figure 4A:
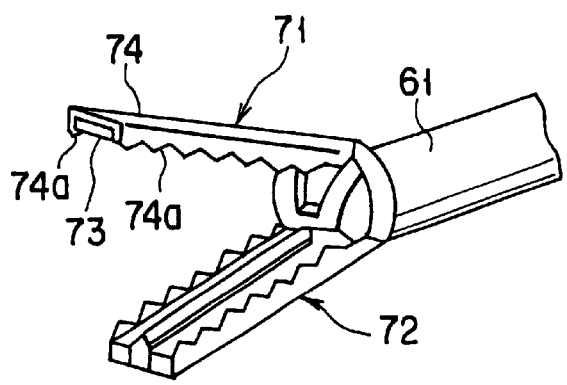
FIG. 4A is a perspective view of a high-frequency treatment tool according to a 2nd embodiment of the present invention.
Figure 4B:
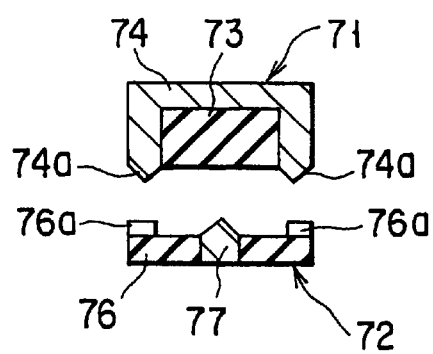
FIG. 4B is a sectional view of a treatment portion of the high-frequency treatment tool shown in FIG. 4A.
Figure 5:
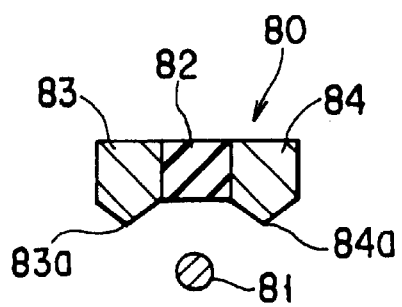
FIG. 5 is a sectional view of a treatment portion of a high-frequency treatment tool according to a 3rd embodiment of the present invention.

FIGS. 4A and 4B show a 2nd embodiment of the present invention. In a high-frequency treatment tool of this embodiment, the arrangement of a second jaw 72 is different from that in the 1st embodiment. More specifically, in this embodiment, the second jaw 72 comprises a main body portion 76 consisting of a material having electrical insulating properties and an electrode portion 77 consisting of a conductive material and arranged almost at the central portion of the main body portion 76 to substantially extend along the total length of the main body portion 76. Serrate gripping portions 76a meshing with gripping portions 74a of a first jaw 71 are formed on both sides of the main body portion 76. The arrangement of the remaining portions is the same as in the 1st embodiment.

According to this arrangement, since the second jaw 72 also has the gripping portions 76a, the tissue gripping area is larger than the 1st embodiment, so tissue can be reliably gripped.

Figure 6:
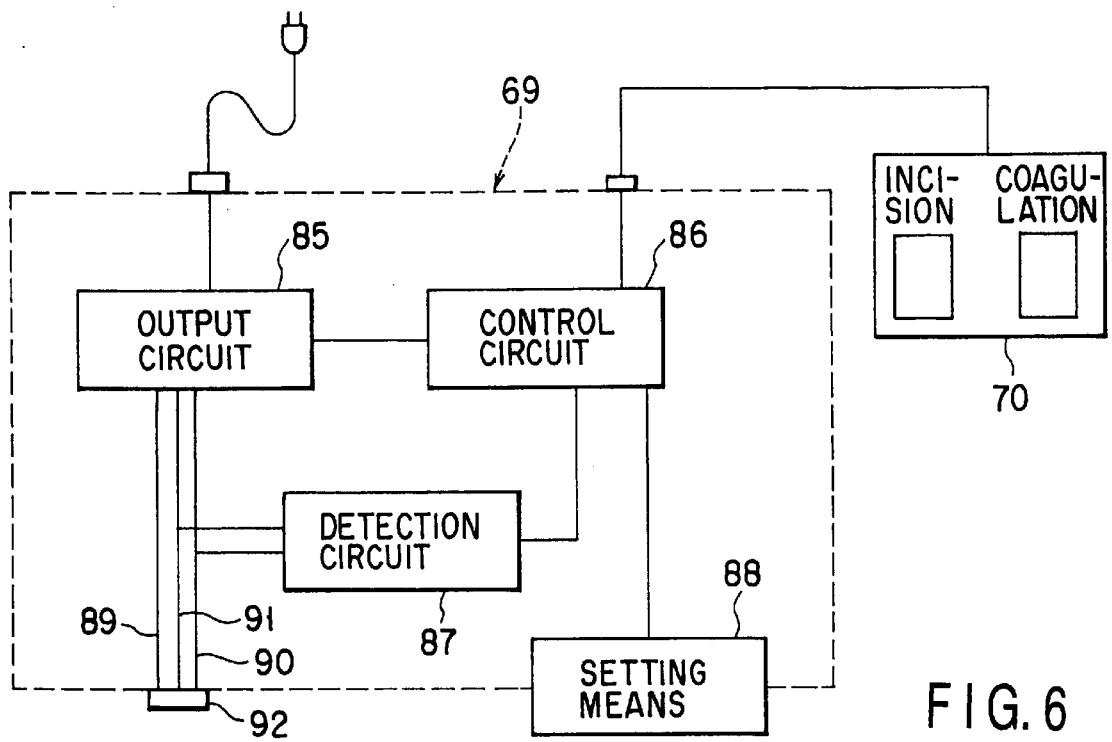
FIG. 6 is a block diagram showing the circuit arrangement of a power supply unit for supplying a high-frequency current to the treatment portion shown in FIG. 5.

FIGS. 5 to 7B show a 3rd embodiment of the present invention. As shown in FIG. 6, a bipolar forceps as a high-frequency treatment tool of this embodiment has a treatment portion comprising a first jaw 80 and a second jaw 81. The first jaw 80 has two electrode portions 83 and 84 electrically insulated from each other by an insulating member 82. In this case, the first electrode portion 83 and second electrode portion 84 are positioned on both sides of the insulating member 82 to sandwich the insulating member 82. The distal ends of the electrode portions 83 and 84 are formed as serrate gripping portions 83a and 84a, respectively. The second jaw 81 comprises a rod consisting of a conductive material and having a circular section and is formed as an electrode portion. The second jaw (electrode portion) 81 is located to come into contact with only the insulating member 82 when the treatment portion is kept closed.

A high-frequency cautery power supply unit 69 for supplying a high-frequency current to the electrode portions 81, 83, and 84 has an arrangement shown in FIG. 6. In FIG. 6, reference numeral 85 denotes an output circuit for supplying a high-frequency current; 86, a control circuit for controlling the high-frequency output from the output circuit 85 in accordance with a control signal from a foot switch 70; 88, a setting means for inputting a predetermined output condition to the control circuit 86 as an electrical signal; 92, a connector to which a power supply cable from the bipolar forceps is connected; 89, 90, and 91, lines for connecting the output circuit 85 to the connector 92 in correspondence with the electrode portions 81, 83, and 84, respectively; and 87, a detection circuit for detecting the high-frequency current flowing through the lines 89, 90, and 91 and sending a detection signal to the line 89. The arrangement of the remaining portions is the same as in the 1st embodiment.

Figure 7A:
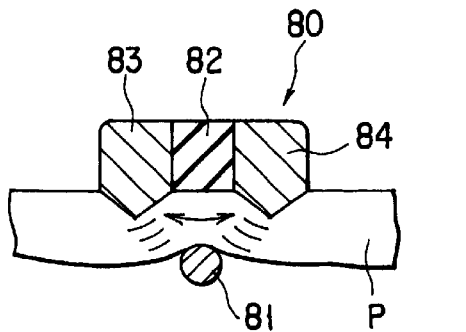
FIGS. 7A and 7B are sectional views showing a way of use of the treatment portion shown in FIG. 5.
Figure 7B:
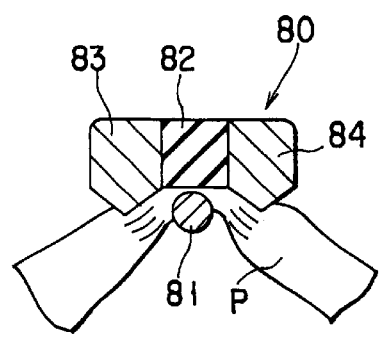

FIGS. 7A and 7B show steps of coagulating/incising tissue P using the bipolar forceps having the above arrangement. FIG. 7A shows a state wherein the tissue P is sandwiched by the first jaw 80 and second jaw 81. Even when the tissue P has a thin film shape, the jaws 80 and 81 to which a high-frequency current is supplied do not come into contact with each other. This is because when the treatment portion is completely closed, the second jaw 81 comes into contact with only the insulating member 82. In this state, a coagulation current is flowed across the two coagulation electrode portions 83 and 84 of the first jaw 80 to coagulate the tissue P.

Upon completing coagulation, the treatment portion is further tightly closed, and the tissue P is pressed against the insulating member 82 by the second jaw 81. In this case as well, the jaws 80 and 81 do not come into contact with each other. In this state, an incision current is flowed across the first electrode portion 83 and the electrode portion (second jaw) 81 and across the second electrode portion 84 and the electrode portion (second jaw) 81 to incise the tissue P.

As described above, in the bipolar forceps of this embodiment, when the treatment portion is completely closed, the second jaw 81 comes into contact with only the insulating member 82 of the first jaw 80. That is, when the tissue is gripped by the jaws 80 and 81, the electrode portions to which a high-frequency current is supplied do not come into contact with each other. Hence, no electrical short circuit occurs between the jaws 8a and 8b, and even thin membranous tissue can be reliably coagulated or incised.

In the bipolar forceps of this embodiment, the insulating member 82 is sandwiched by the two electrode portions 83 and 84 of the first jaw 80, and the tissue is also gripped by this insulating member 82. Hence, the operator can reliably grip the tissue without missing it and coagulate/incise it.

In this embodiment, the three lines 89, 90, and 91 corresponding to the electrode portions 81, 83, and 84, respectively, are arranged in the high-frequency cautery power supply unit 69. Hence, the switch for switching between incision and coagulation need not be provided on the operation portion side of the bipolar forceps.

When coagulating vital tissue using a bipolar forceps that is formed by making the two electrode portions 83 and 84 function as one electrode, and the other electrode portion 81 function as the other electrode, where the vital tissue is gripped between the two electrode portions 83, 84 and the other electrode portion 81, the effective electrode surface of the other electrode portion 81, which actually touches the vital tissue, is smaller than that of the two electrode portions 83 and 84. Accordingly, a current concentrates on the other electrode portion 81, thereby enabling an efficient coagulation treatment and incision treatment and enabling a local treatment. This treatment tool can also perform the coagulation treatment and the incision treatment continuously, while gripping vital tissue.

Figure 8:
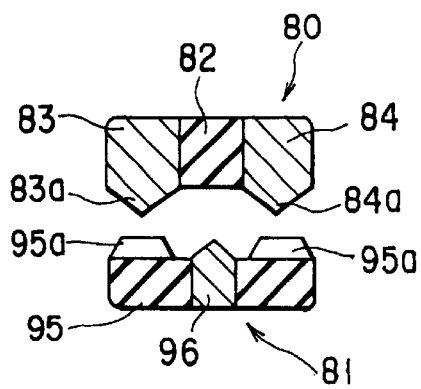
FIG. 8 is a sectional view of a treatment portion of a high-frequency treatment tool according to a 4th embodiment of the present invention.

FIG. 8 shows a 4th embodiment of the present invention. In a high-frequency treatment tool of this embodiment, the arrangement of a second jaw 81 is different from that in the 3rd embodiment. More specifically, the second jaw 81 comprises a main body portion 95 consisting of a material having electrical insulating properties, and an electrode portion 96 consisting of a conductive material and arranged almost at the central portion of the main body portion 95 to substantially extend throughout the total length of the main body portion 95. Serrate gripping portions 95a meshing with gripping portions 83a and 84a of a first jaw 80 are formed on both sides of the main body portion 95. The arrangement of the remaining portions is the same as in the 3rd embodiment.

According to this arrangement, since the second jaw 81 also has the gripping portions 95a, the tissue gripping area is larger than the 3rd embodiment, so tissue can be reliably gripped.

Figure 9A:
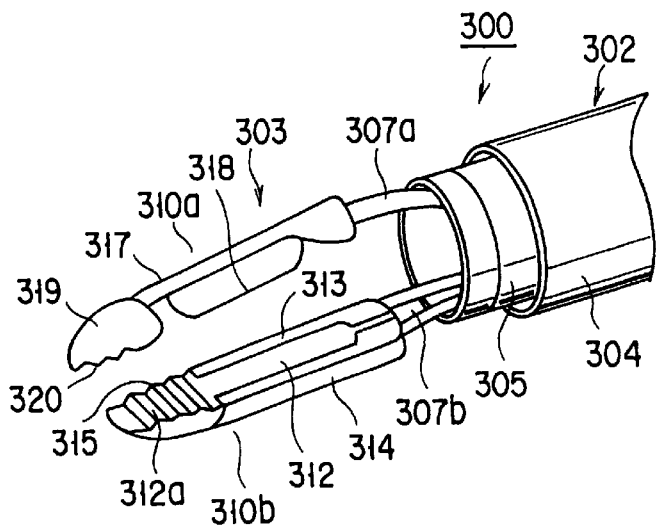
FIG. 9A is a perspective view of the treatment portion of a high-frequency treatment tool according to a 5th embodiment of the present invention.
Figure 9B:
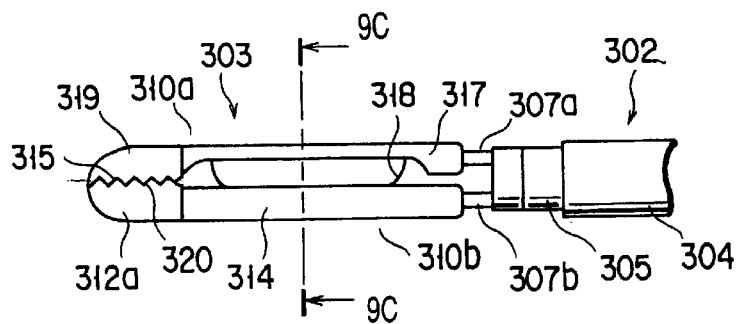
FIG. 9B is a side view of the treatment portion shown in FIG. 9A.
Figure 9C:
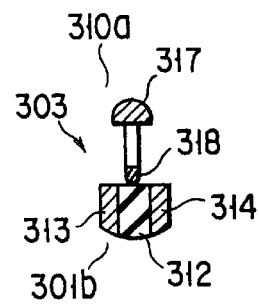
FIG. 9C is a sectional view taken along line 9C—9C in FIG. 9B.

FIGS. 9A to 9C show a 5th embodiment of the present invention. As shown in FIGS. 9A to 9C, a bipolar forceps 300 as a high-frequency treatment tool of this embodiment comprises a long insertion portion 302 to be inserted into the body cavity of a patient, a treatment portion 303 attached to the distal end portion of the insertion portion 302 to grip vital tissue and coagulate or incise it, and an operation portion (not shown) coupled to the proximal end portion of the insertion portion 302.

The insertion portion 302 is comprised of a rotatable outer sheath 304 and an inner sheath 305 inserted in the outer sheath 304 to move back and forth. The inner sheath 305 is moved back and forth by operating the operation portion. A holding member having electrical insulating properties is fitted in the inner sheath 305. A pair of elastic members 307a and 307b are stationarily held by the holding member. The elastic members 307a and 307b are comprised of conductive rods formed from spring steel or the like. Each conductive rod is covered with an insulating tube. The proximal end portions of the conductive rods of the elastic members 307a and 307b are connected to a connector receptacle (not shown) of the operation portion, and the distal end portions are projected from the distal end of the inner sheath 305. The elastic members 307a and 307b have first and second jaws 310a and 310b at their distal ends, respectively, and always bias the jaws 310a and 310b in the opening direction.

In this arrangement, when the operation portion is operated in a predetermined direction, the inner sheath 305 moves forward in the axial direction, and the elastic members 307a and 307b are relatively retracted into the inner sheath 305 (see FIG. 9B). At this time, the elastic members 307a and 307b are pressed inward by the inner wall of the inner sheath 305 to close the jaws 310a and 310b. When the operation portion is operated in the opposite direction, the elastic members 307a and 307b relatively project from the inner sheath 305, and the jaws 310a and 310b are opened by the restoring force of the elastic members 307a and 307b (see FIG. 9A).

The second jaw 310b has two coagulation electrode portions 313 and 314 electrically insulated from each other by an insulating member 312. The first and second coagulation electrode portions 313 and 314 are positioned on both sides of the insulating member 312 to sandwich the insulating member 312 therebetween. A distal end portion 312a of the insulating member 312 extends from the distal end sides of the two electrode portions 313 and 314. A serrate uneven portion 315 is formed on the surface (surface opposing the first jaw 310a) of the distal end portion 312a.

The first jaw 310a comprises a main body portion 317 extending opposite to the second jaw 310b, a wire-shaped or hard-rod-shaped incision electrode portion 318 extending in the longitudinal direction of the main body portion 317 almost at the central portion of the main body portion 317 and projecting in a U shape from the main body portion 317 to the second jaw 310b side, and a gripping element 319 provided at the distal end portion of the main body portion 317 and opposing the distal end portion 312a of the insulating member 312 of the second jaw 310b. In this case, the incision electrode portion 318 comes into contact with only the insulating member 312 when the jaws 310a and 310b (treatment portion 303) are closed. The gripping element 319 is made of a material having electrical insulating properties and has, on its surface (surface opposing the second jaw 310b), a serrate uneven portion 320 meshing with the uneven portion 315 of the distal end portion 312a of the insulating member 312.

As described above, in the bipolar forceps 300 of this embodiment, when the treatment portion 303 is completely closed, the incision electrode portion 318 of the first jaw 310a comes into contact with only the insulating member 312 of the second jaw 310b. That is, when tissue is gripped, the conductive portions of the jaws 310a and 310b to which a high-frequency current is supplied do not come into contact with each other. Since no electrical short circuit occurs between the jaws 310a and 310b, even thin membranous tissue can be reliably coagulated or incised.

In the bipolar forceps 300 of this embodiment, the insulating member 312 is inserted between the two electrode portions 313 and 314 of the second jaw 310b, and the tissue can also be gripped by the insulating member 312. Hence, the operator can reliably grip the tissue without missing it and coagulate/incise it. Especially, in this embodiment, since the distal end portion 312a of the insulating member 312 and the gripping element 319 extend to project forward from the electrode portions 313, 314, and 318, and the uneven portions 315 and 320 are formed on the surfaces (part of the gripping surfaces for gripping tissue) of the distal end portion 312a and gripping element 319, the gripping area increases, and the tissue can be reliably gripped without any slip.

In this embodiment, only one of the gripping element 319 and the distal end portion 312a need be made of an insulating material. The gripping element 319 and distal end portion 312a need not be wholly formed from the insulating material. For example, the surfaces of the gripping element 319 and distal end portion 312a may be coated with Teflon or a ceramic.

Further, when coagulating vital tissue, the treatment tool may be used as a bipolar forceps that is formed by making the two electrode portions 313 and 314 function as one electrode, and the electrode portion 318 function as the other electrode opposed to the one electrode. In this case, when vital tissue is gripped between the two electrode portions 313, 314 and the other electrode portion 318, the effective electrode surface of the other electrode portion 318, which actually touches the vital tissue, is smaller than that of the two electrode portions 313 and 314. Accordingly, a current concentrates on the other electrode portion 318, thereby enabling an efficient coagulation treatment and incision treatment. This treatment tool can also perform the coagulation treatment and the incision treatment continuously, while gripping vital tissue.

Figure 10:
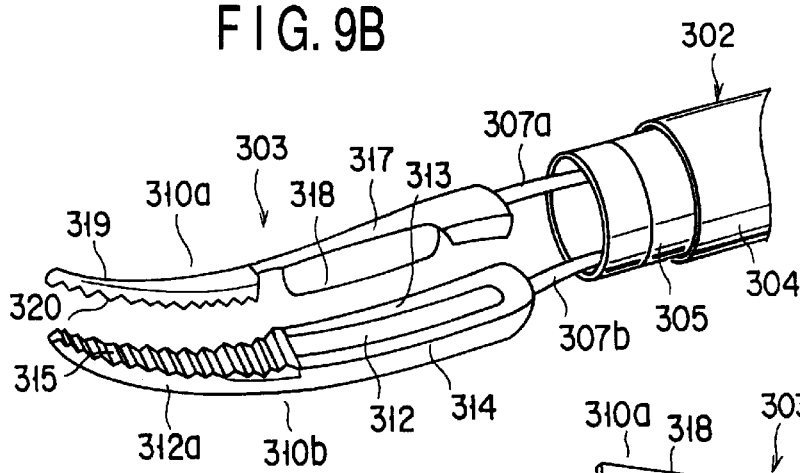
FIG. 10 is a perspective view of a treatment portion of a high-frequency treatment tool according to a 6th embodiment of the present invention.

FIG. 10 shows a 6th embodiment. The first and second jaws 310a and 310b are formed as a Kelly clamp portion curved to one side. The arrangement of the remaining portions is the same as in the 5th embodiment.

Figure 11:
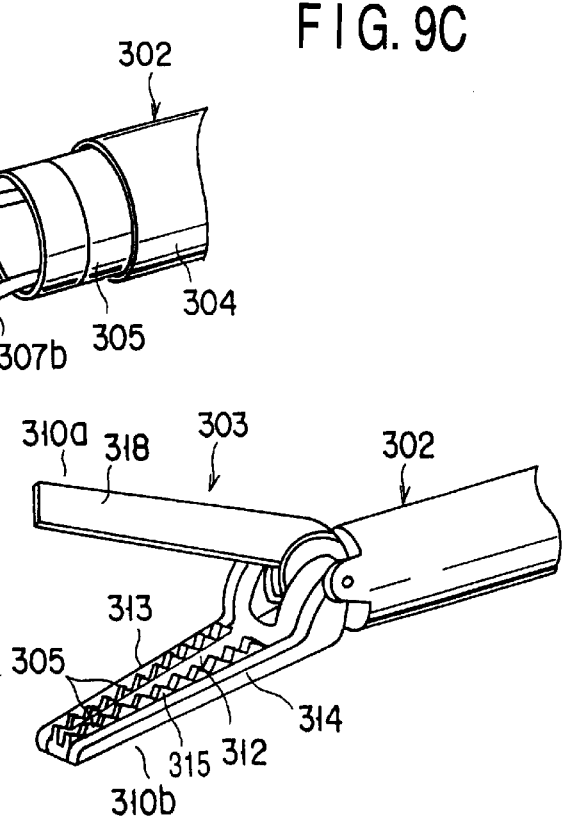
FIG. 11 is a perspective view of a treatment portion of a high-frequency treatment tool according to a modification of the 6th embodiment.

In the 5th embodiment, the uneven portions 315 and 320 are formed partially on the gripping surfaces of the jaws 310a and 310b. In FIG. 11 showing a modification of the 6th embodiment, the uneven portion 315 is formed throughout the total length of the insulating member 312 of the second jaw 310b. More specifically, the serrate uneven portion 315 is formed on both sides of the gripping surface of the second jaw 310b throughout the total length. In FIG. 11, although the treatment portion 303 is slightly different from the treatment portion (jaws 310a and 310b) of the 5th embodiment, the same reference numerals as in the 5th embodiment denote the same parts.

Figure 12B:
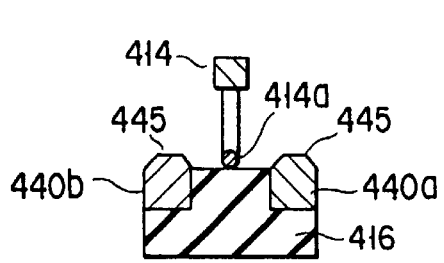
FIG. 12B is a sectional view taken along line 12B—12B in FIG. 12A.
Figure 12A:
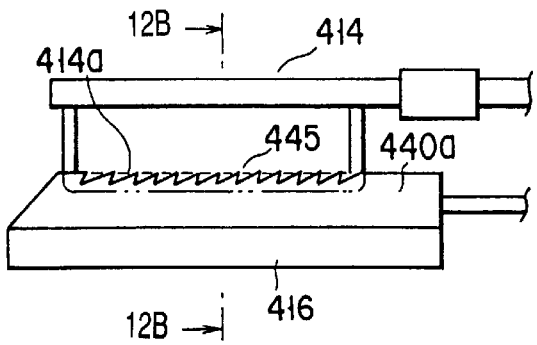
FIG. 12A is a side view of a treatment portion of a high-frequency treatment tool according to a 7th embodiment of the present invention.

FIGS. 12A and 12B show a 7th embodiment of the present invention.

In this embodiment, serrate uneven portions 445 are formed on the coagulation surfaces of first and second coagulation electrodes 440a and 440b. When the uneven portions 445 are formed on the coagulation surfaces, vital tissue A can be prevented from escaping to the far-end side of a treatment portion 403 during coagulation or incision. Hence, the target portion of the vital tissue A can be reliably gripped.

In DE 4032471 C2 described above as a prior art, the incision electrode and the pair of coagulation electrodes of the gripping portion of the high-frequency treatment tool are formed by bending a wire. Hence, the incision electrode and coagulation electrodes may short-circuit due to twist or deformation of the distal end portion of the high-frequency treatment tool, or the target portion at the center of the coagulation range cannot be incised when the incision electrode is closed, and bleeding may occur. FIG. 10 of Jpn. Pat. Appln. KOKAI Publication No. 10-000199 shows a structure in which an insulating member is inserted between the electrodes. However, the same problem as described above is posed because the incision electrode does not align with the center of the insulating member during incision.

Figure 13:
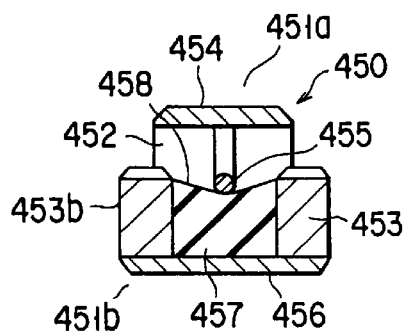
FIG. 13 is a sectional view of the treatment portion of a high-frequency treatment tool according to an 8th embodiment of the present invention.
Figure 14A:
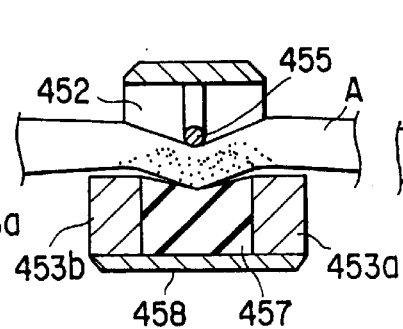
FIGS. 14A and 14B are sectional views showing a way of use of the high-frequency treatment tool shown in FIG. 13.
Figure 14B:
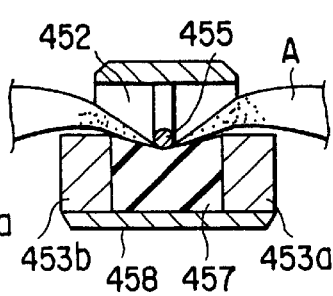

FIGS. 13, 14A, and 14B show an 8th embodiment capable of solving this problem.

A first jaw 451a constituting a gripping portion 450 for gripping vital tissue A has an incision electrode 452 as the first electrode. A second jaw 451b has first and second coagulation electrodes 453a and 453b as the second electrodes. The incision electrode 452 is constituted by a plate element 454 with its surface coated with an insulating material, and a conductive wire 455 formed by bending a metal wire or the like into a substantially U shape and fixing the two end portions to the front and rear ends of the plate element 454.

The second jaw 451b is constituted by a plate element 456 with its surface being coated with an insulating material, and an insulating member 457 consisting of a ceramic or a synthetic resin material and fixed at the central portion of the plate element 456. The first and second coagulation electrodes 453a and 453b are fixed on both sides of the insulating member 457. That is, the first and second coagulation electrodes 453a and 453b are electrically insulated from each other by the insulating member 457.

The upper surface of the insulating member 457 is substantially flush with the coagulation surfaces of the first and second coagulation electrodes 453a and 453b. A wide-angled V-shaped guide portion 458 for guiding the incision electrode 452 is formed on the upper surface of the insulating member 457. When the first and second jaws 451a and 451b are closed, the incision electrode 452 is aligned to the axial center between the first and second coagulation electrodes 453a and 453b.

The function of a 9th embodiment will be now described with reference to FIGS. 14A and 14B.

As shown in FIG. 14A, when vital tissue A to be treated is sandwiched and gripped by the first and second jaws 451a and 451b, the vital tissue A is gripped between the incision electrode 452 and the first and second coagulation electrodes 453a and 453b including the insulating member 457. Since the wide-angled V-shaped guide portion 458 is formed on the upper surface of the insulating member 457, the vital tissue A has also a wide-angled V shape along the guide portion 458.

In this state, when a high-frequency current is flowed from a high-frequency cautery power supply unit, a coagulation current flows across the first coagulation electrode 453a and the second coagulation electrode 453b to coagulate the vital tissue A. Subsequently, when an incision current is flowed across the incision electrode 452 and the first and second coagulation electrodes 453a and 453b, and the incision electrode 452 and first and second coagulation electrodes 453a and 453b are further closed, the coagulated vital tissue A is incised by the incision electrode 452.

At this time, the incision electrode 452 is aligned to the center between the first and second coagulation electrodes 453a and 453b by the guide portion 458 formed on the upper surface of the insulating member 457. That is, even when the incision electrode 452 slightly deforms to the left or right, the position of the conductive wire 455 is corrected by the guide portion 458 to the center between the first and second coagulation electrodes 453a and 453b. Hence, the short circuit between the incision electrode 452 and the first and second coagulation electrodes 453a and 453b can be prevented, and the target portion of the vital tissue A can be reliably incised.

Figure 15A:
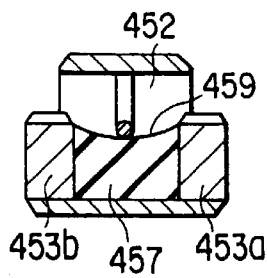
FIGS. 15A to 15C are sectional views showing a 9th embodiment of the present invention.
Figure 15B:
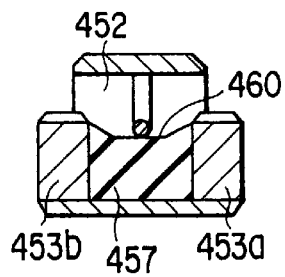
Figure 15C:
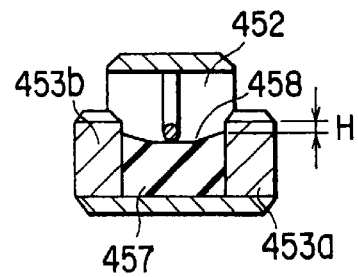

In this embodiment, the wide-angled V-shaped guide portion 458 is formed on the upper surface of the insulating member 457. However, a recessed arcuated guide portion 459 may be formed, as shown in FIG. 15A. Alternatively, an inverted trapezoidal guide portion 460 may be formed, as shown in FIG. 15B. In FIG. 15C, the coagulation surfaces of the first and second coagulation electrodes 453a and 453b are set at slightly higher level than the upper surface of the insulating member 457 to form a step difference H. With this arrangement, a tensile force is applied to the vital tissue A, so the vital tissue A can be easily incised, and the incisional wound can be easily separated from the incision electrode 452.

Further, the forceps of this embodiment may be used as a bipolar forceps that is formed by making the two electrode portions 453a and 453b function as one electrode, and the electrode portion 455 function as the other electrode opposed to the one electrode.

Figures 16A, 16B, 16C:
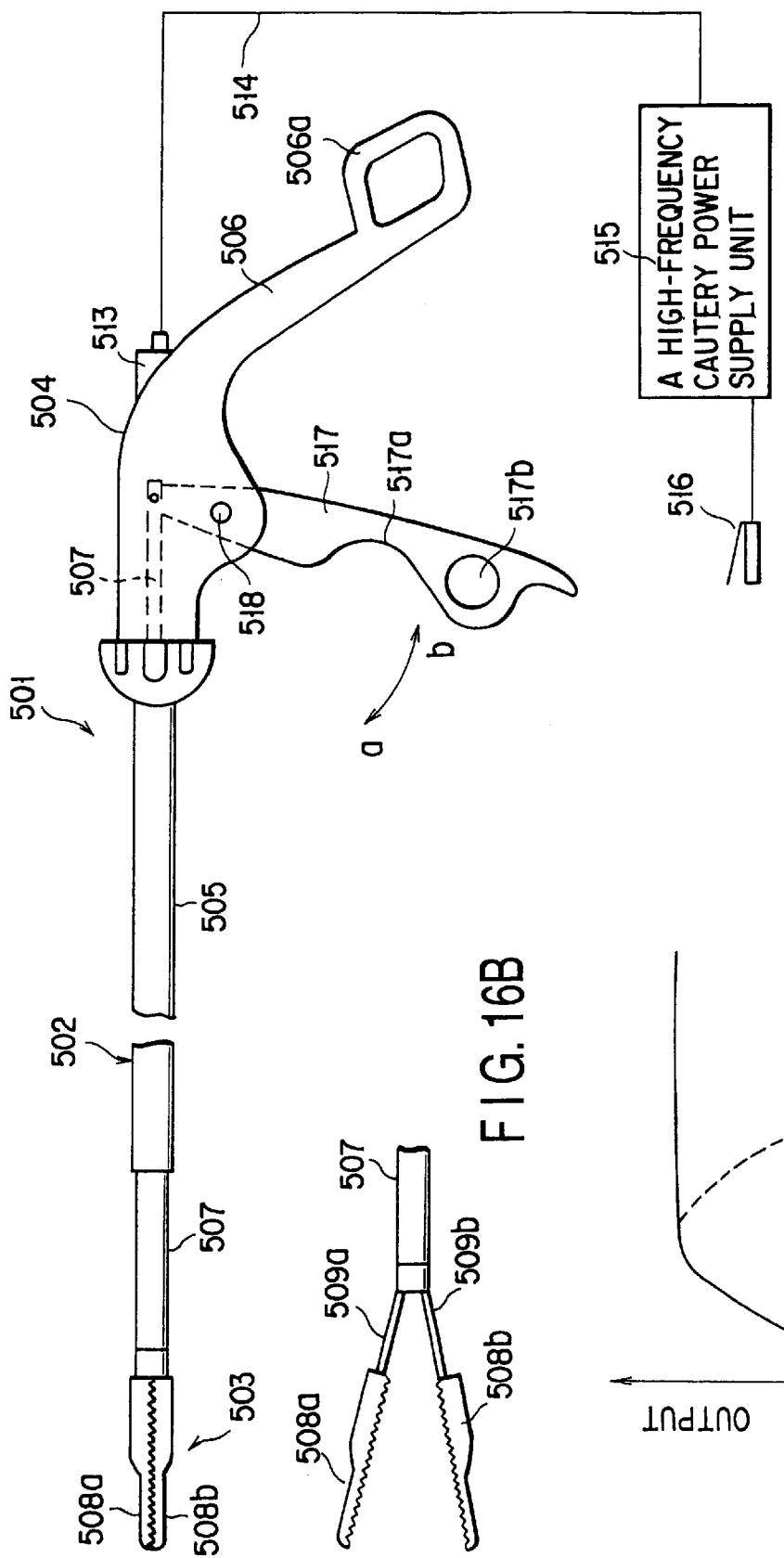
FIG. 16A is a side view showing the overall arrangement of a high-frequency treatment tool according to a 10th embodiment of the present invention.
FIG. 16B is a side view of a treatment portion of the high-frequency treatment tool shown in FIG. 16A in the open state.
FIG. 16C is a graph showing the relationship between the output and the impedance.

FIGS. 16A to 17B show a 10th embodiment of the present invention. As shown in FIGS. 16A to 16C, a bipolar forceps 501 as a high-frequency treatment tool comprises a long insertion portion 502 to be inserted into the body cavity of a patient, a treatment portion 503 attached to the distal end portion of the insertion portion 502 to grip vital tissue and coagulate or incise it in the body cavity, to which power can be supplied, and an operation portion 504 coupled to the proximal end portion of the insertion portion 402.

The insertion portion 502 has a rotatable outer sheath 505. An inner sheath 507 of the outer sheath 505 is inserted in a grip 506 constituting the operation portion 504. The treatment portion 503 has a long rod (not shown) inserted in the outer sheath 505. At the distal end portion of the rod, a pair of jaws 508a and 508b as electrodes constituting the treatment portion 503 are fixed to elastic members 509a and 509b for biasing the jaws 508a and 508b in the opening direction. The elastic members 509a and 509b are formed from spring steel or the like and covered with insulating members.

Figure 17A:
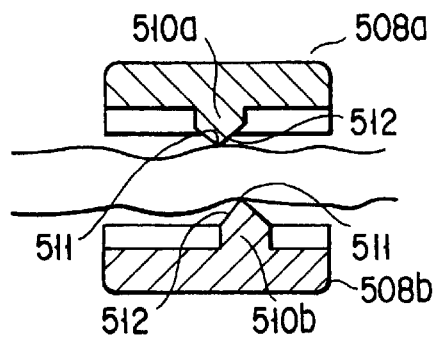
FIG. 17A is a sectional view showing a state wherein tissue is gripped by the treatment portion of the high-frequency treatment tool shown in FIG. 16A.
Figure 17B:
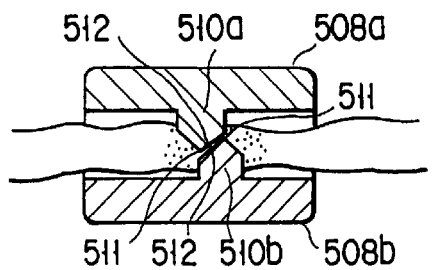
FIG. 17B is a sectional view showing a state wherein tissue is coagulated/incised by the high-frequency treatment tool shown in FIG. 16A.

As shown in FIGS. 17A and 17B, the jaws 508a and 508b have serrate portions which mesh with each other when the jaws 508a and 508b are closed, so vital tissue A can be reliably gripped. Incision projections 510a and 510b as projecting portions are integrated with the jaws 508a and 508b along the longitudinal direction at substantially middle portions in the direction of width of the mesh portions of the jaws 508a and 508b.

Each of the incision projections 510a and 510b has a substantially V-shaped section and an acute-angled portion 511 at the distal end portion and oblique surfaces 512 on both sides of the distal end portion. The incision projection 510a on the jaw 508a side is formed at the middle portion in the direction of width of the jaw 508a. The incision projection 510b on the jaw 508b side is shifted to one side in the direction of width of the jaw 508b. When the jaws 508a and 508b are closed, the acute-angled portions 511 do not abut against each other. Instead, the incision projections 510a and 510b lap to joint the right and left oblique surfaces 512 with each other.

As shown in FIGS. 16A to 16C, a conductive member (not shown) connected to the jaws 508a and 508b of the treatment portion 503 is connected to a connector receptacle 513 of the operation portion 504 through the outer sheath 505 of the insertion portion 502. The connector receptacle 513 is connected to a high-frequency cautery power supply unit 515 through a cable 514. The high-frequency cautery power supply unit 515 has a foot switch 516.

The grip 506 has a trigger 517 as a forceps operation means. The trigger 517 is coupled to the upper end portion of the grip 506 to freely pivot about a pivot pin 518. The upper end portion of the pivot fulcrum of the trigger 517 is coupled to the proximal end portion of the inner sheath 507.

The grip 506 has a finger hook portion 506a on which the operator places the thumb. The trigger 517 has finger hook portions 517a and 517b on which the operator places the index and middle fingers, respectively. When the trigger 517 is opened in a direction indicated by an arrow a, the inner sheath 507 moves backward to open the jaws 508a and 508b. When the trigger 517 is closed in a direction indicated by an arrow b, the inner sheath 507 moves forward to close the jaws 508a and 508b.

The function of the 10th embodiment will be described.

The cable 514 is connected to the connector receptacle 513 of the bipolar forceps 501 to electrically connect the bipolar forceps 501 to the high-frequency cautery power supply unit 515. In the initial state, the trigger 517 of the operation portion 504 is pivoted to the direction indicated by the arrow a. In this state, the pair of elastic members 509a and 509b of the treatment portion 503 project from the inner sheath 507 to open the jaws 508a and 508b, as shown in FIG. 16B.

When the finger hook portions 517a and 517b of the trigger 517 are pulled to the grip 506 side against the spring force of the biasing members in the grip 506, the inner sheath 507 moves forward in the axial direction. As the inner sheath 507 moves forward, the elastic members 509a and 509b are relatively retracted into the inner sheath 507 to close the jaws 508a and 508b, as shown in FIG. 16A.

In this state, the insertion portion 502 of the bipolar forceps 501 is inserted into the body of a patient, and the treatment portion 503 at the distal end of the insertion portion 502 is placed near the vital tissue A to be treated in the body. When the trigger 517 is released, the trigger 517 returns to the home position by the spring force of the biasing member in the grip 506. The elastic members 509a and 509b relatively project from the inner sheath 507, and the jaws 508a and 508b are opened by the elastic restoring force of the elastic members 509a and 509b.

After the vital tissue A is inserted between the opened jaws 508a and 508b, the finger hook portions 517a and 517b of the trigger 517 are pulled to the grip 506 side to move the inner sheath 507 forward in the axial direction. As the inner sheath 507 moves forward, the elastic members 509a and 509b are relatively retracted into the inner sheath 507 to close the jaws 508a and 508b. The vital tissue A is gripped between the pair of jaws 508a and 508b, as shown in FIG. 17A.

Since the jaws 508a and 508b have serrate portions which mesh with each other when the jaws 508a and 508b are closed, the vital tissue A is reliably gripped. In this state, a high-frequency current flows from the high-frequency cautery power supply unit 515 to the connector receptacle 513 through the cable 514. A coagulation current flows across the jaws 508a and 508b to coagulate the vital tissue A.

Subsequently, when the finger hook portions 517a and 517b of the trigger 517 are further pulled to the grip 506 side, the jaws 508a and 508b are further closed, and an incision current flows across the jaws 508a and 508b. The incision projections 510a and 510b move close to each other.

Since the incision projections 510a and 510b lap to joint the oblique surfaces 512 with each other without making the acute-angled portions 511 abut against each other, the vital tissue A is incised by the pair of jaws 508a and 508b, as shown in FIG. 17B.

The coagulation current generally has load characteristics representing that when the impedance of the vital tissue A increases upon coagulation, the output decreases, as indicated by the broken line in FIG. 16C. In this embodiment, however, power control is performed in a constant power output mode in which even when the impedance increases, the output does not decrease, as indicated by the solid line in FIG. 16C. Hence, power can be concentrated in a short time to incise the vital tissue A. That is, incision can be performed simultaneously with coagulation without switching between the coagulation current and the incision current.

When coagulation and incision are complete, the trigger 517 is pivoted in the direction indicated by the arrow a. The inner sheath 507 moves backward, and the elastic members 509a and 509b are opened by the elastic restoring force. The jaws 508a and 508b are released from the vital tissue A.

To peel the vital tissue A, while the jaws 508a and 508b are closed using the trigger 517, and the distal end portions of the jaws 508a and 508b are pressed against the portion of the vital tissue A to be peeled, the trigger 517 is pivoted in the direction indicated by the arrow a. The inner sheath 507 moves backward, and the jaws 508a and 508b are opened by the elastic restoring force of the elastic members 509a and 509b. By repeatedly opening/closing the jaws 508a and 508b, the vital tissue A can be peeled.

According to this embodiment, gripping, coagulation, and incision of the vital tissue A can be performed by one bipolar forceps 501. Cumbersome exchange of the bipolar forceps 501 can be reduced during the operation to shorten the operation time. In addition, the tissue can be easily coagulated/incised by the series of operations of the operation portion 504 without any mechanical switching for tissue coagulation and incision.

In this embodiment as well, an electrical insulating portion may be formed on the gripping surface of at least one gripping portion (jaw 508a or 508b). In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions. In addition, an abutment portion 121 may be formed on the trigger 517, and a projecting portion 120 may be formed on the grip 506. When the projecting portion 120 abuts against the abutment portion 121, the treatment portion 503 is not closed anymore, and a predetermined gap C is formed between the first jaw 508a and the second jaw 508b.

Figure 18:
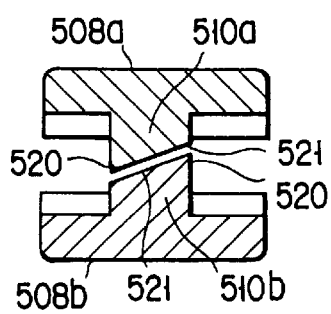
FIG. 18 is a sectional view of a treatment portion of a high-frequency treatment tool according to an 11th embodiment of the present invention.

FIG. 18 shows an 11th embodiment of the present invention. In this embodiment, the distal end portions of incision projections 510a and 510b are formed into a knife-edge shape. An acute-angled portion 520 is formed at the distal end portion, and an oblique surface 521 is formed on one side. When jaws 508a and 508b are closed, the acute-angled portions 520 do not abut against each other. Instead, the incision projections 510a and 510b lap to joint the right and left oblique surfaces 512 with each other.

Figure 19:
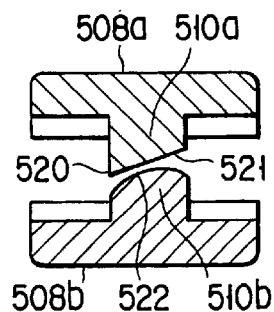
FIG. 19 is a sectional view of a treatment portion of a high-frequency treatment tool according to a 12th embodiment of the present invention.

FIG. 19 shows a 12th embodiment of the present invention. In this embodiment, the distal end portion of one incision projection 510a is formed into a knife-edge shape.

An acute-angled portion 520 is formed at the distal end portion, and an oblique surface 521 is formed on one side. The distal end portion of the other incision projection 510*b* is formed into an arcuated portion 522. When jaws 508*a* and 508*b* are closed, the acute-angled portions 520 do not abut against the arcuated portion 522. Instead, the incision projections 510*a* and 510*b* lap to joint the oblique surface 512 with the arcuated portion 522.

Figure 20:
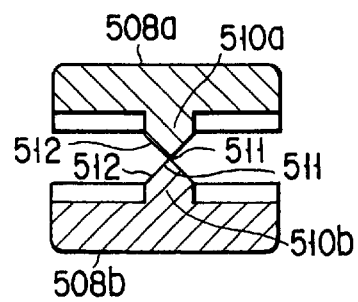
FIG. 20 is a sectional view of a treatment portion of a high-frequency treatment tool according to a 13th embodiment of the present invention.

FIG. 20 shows a 13th embodiment of the present invention. In this embodiment, each of incision projections 510*a* and 510*b* has a substantially V-shaped section and an acute-angled portion 511 at the distal end portion and oblique surfaces 512 on both sides of the acute-angled portion 511. The incision projections 510*a* and 510*b* oppose each other. When jaws 508*a* and 508*b* are closed, the acute-angled portions 511 abut against each other to incise tissue. This embodiment is effective to incise a thin film or the like because the acute-angled portions 511 abut against each other.

Figure 21:
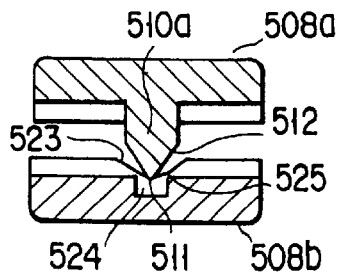
FIG. 21 is a sectional view of a treatment portion of a high-frequency treatment tool according to a 14th embodiment of the present invention.

FIG. 21 shows a 14th embodiment of the present invention. In this embodiment, one incision projection 510*a* has a substantially V-shaped section and an acute-angled portion 511 at the distal end portion and oblique surfaces 512 on both sides of the acute-angled portion 511. A jaw 508*b* has a wide-angled V-shaped groove 523 and a recessed groove 524 continuously formed at the bottom portion of the wide-angled V-shaped groove 523. Edge portions 525 are formed between the wide-angled V-shaped groove 523 and the recessed groove 524. When jaws 508*a* and 508*b* are closed, the acute-angled portion 511 of one incision projection 510*a* enters the recessed groove 524, and the two oblique surfaces 512 simultaneously abut against the edge portions 525 to incise tissue.

Figure 22:
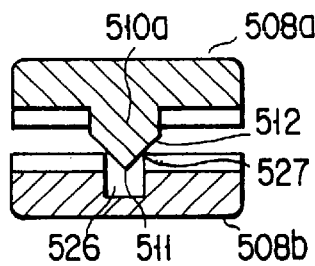
FIG. 22 is a sectional view of a treatment portion of a high-frequency treatment tool according to a 15th embodiment of the present invention.

FIG. 22 shows a 15th embodiment of the present invention. In this embodiment, one incision projection 510*a* has a substantially V-shaped section and an acute-angled portion 511 at the distal end portion and oblique surfaces 512 on both sides of the acute-angled portion 511. A jaw 508*b* has a recessed groove 526. Edge portions 527 are formed at the edges of the recessed groove 526. When jaws 508*a* and 508*b* are closed, the acute-angled portion 511 of one incision projection 510*a* enters the recessed groove 526, and the two oblique surfaces 512 simultaneously abut against the edge portions 527 to incise tissue.

According to the 14th and 15th embodiments, by forming the recessed grooves 524 and 526 in the jaws 508*b*, respectively, the tissue contact area can be decreased, and the current density can be increased.

Figure 23:
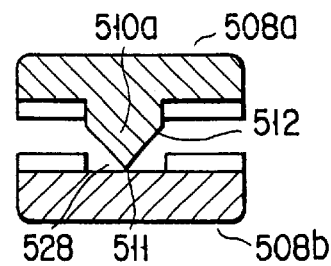
FIG. 23 is a sectional view of a treatment portion of a high-frequency treatment tool according to a 16th embodiment of the present invention.

FIG. 23 shows a 16th embodiment of the present invention. In this embodiment, one incision projection 510*a* has a substantially V-shaped section and an acute-angled portion 511 at the distal end portion and oblique surfaces 512 on both sides of the acute-angled portion 511. A jaw 508*b* has a flat surface 528. When jaws 508*a* and 508*b* are closed, the acute-angled portion 511 of one incision projection 510*a* abuts against the flat surface 528 to incise tissue. A projecting arcuated surface may be formed in place of the flat surface 528.

FIGS. 24A to 27C show a 17th embodiment of the present invention. The same reference numerals as in the 10th embodiment denote the same parts in the 17th embodiment, and a detailed description thereof will be omitted.

Figures 24A, 24B, 24C, 24D:
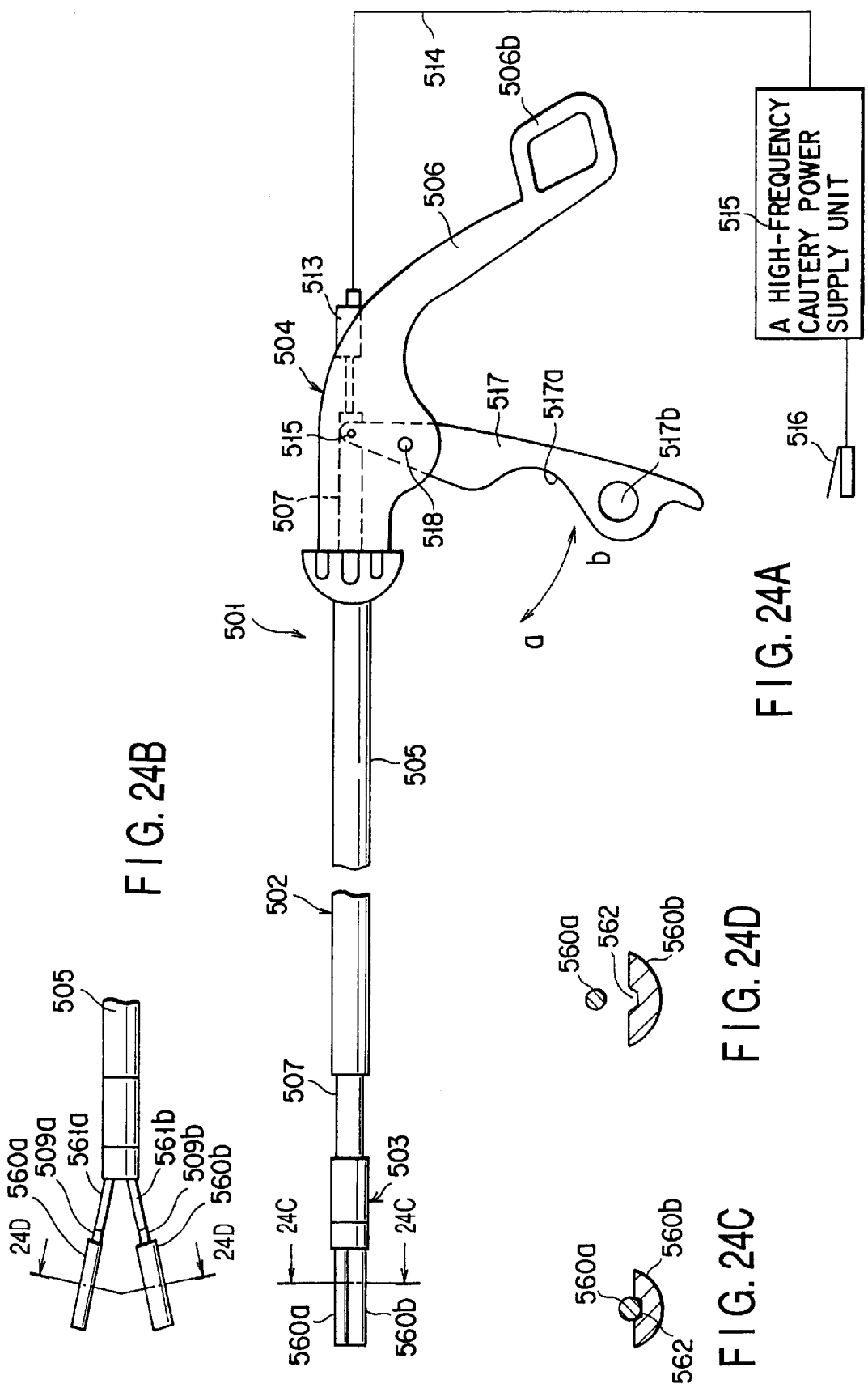
FIG. 24A is a side view of a high-frequency treatment tool according to a 17th embodiment of the present invention.
FIG. 24B is a side view of the high-frequency treatment tool shown in FIG. 24A in the open state.
FIG. 24C is a sectional view taken along a line 24C—24C in FIG. 24A.
FIG. 24D is a sectional view taken along a line 24D—24D in FIG. 24B.

FIG. 24A is a view showing the overall arrangement of a high-frequency treatment tool as an endoscopic operation tool. As shown in FIG. 24A, a bipolar forceps 501 as a high-frequency treatment tool comprises a long insertion portion 502 to be inserted into the body cavity of a patient, a treatment portion 503 attached to the distal end portion of the insertion portion 502 to grip vital tissue and coagulate or incise it in the body cavity, to which power can be supplied, and an operation portion 504 coupled to the proximal end portion of the insertion portion 502.

The insertion portion 502 has a rotatable outer sheath 505. An inner sheath 507 of the outer sheath 505 is inserted in a grip 506 constituting the operation portion 504. The treatment portion 503 has a long rod (not shown) inserted in the outer sheath 505. At the distal end portion of the rod, a pair of jaws 560*a* and 560*b* as electrodes constituting the treatment portion 503 are fixed to elastic members 509*a* and 509*b* for biasing the jaws 560*a* and 560*b* in the opening direction. The elastic members 509*a* and 509*b* are formed from spring steel or the like and covered with insulating tubes 561*a* and 561*b*, respectively.

Figure 25B:
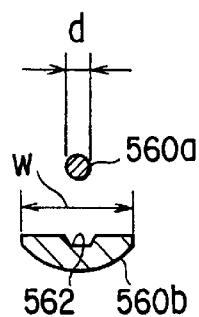
FIG. 25B is a sectional view taken along a line 25B—25B in FIG. 25A.
Figure 25A:
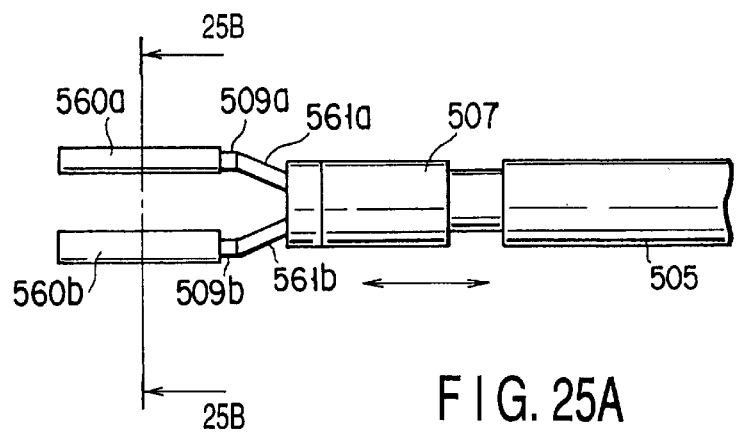
FIG. 25A is a side view of the distal end side of the high-frequency treatment tool shown in FIG. 24A.

As shown in FIGS. 25A and 25B, of the pair of jaws 560*a* and 560*b*, the upper jaw 560*a* is a wire-shaped electrode having a diameter d of 0.5 to 2.5 mm and, more preferably, 1 to 2 mm and capable of simultaneously coagulating and incising vital tissue A. The lower jaw 560*b* has a flat plate shape. A width w of the tissue gripping surface is about 5 mm, and a recessed groove 562 in which the upper jaw 560*a* can fit is formed at almost the central portion of the tissue gripping surface.

A conductive member (not shown) connected to the jaws 560*a* and 560*b* of the treatment portion 503 is connected to a connector receptacle 513 of the operation portion 504 through the outer sheath 505 constituting the insertion portion 502. The connector receptacle 513 is connected to a high-frequency cautery power supply unit 515 through a cable 514. The high-frequency cautery power supply unit 515 has a foot switch 516.

The grip 506 has a trigger 517 as a forceps operation means. The trigger 517 is coupled to the upper end portion of the grip 506 to freely pivot about a pivot pin 518. The upper end portion of the pivot fulcrum of the trigger 517 is coupled to the proximal end portion of the inner sheath 507.

The grip 506 has a finger hook portion 506*a* on which the operator places the thumb. The trigger 517 has finger hook portions 517*a* and 517*b* on which the operator places the index and middle fingers, respectively. When the trigger 517 is opened in a direction indicated by an arrow a, the inner sheath 507 moves backward to open the jaws 560*a* and 560*b*. When the trigger 517 is closed in a direction indicated by an arrow b, the inner sheath 507 moves forward to close the jaws 560*a* and 560*b*.

The function of the 17th embodiment will be described.

The cable 514 is connected to the connector receptacle 513 of the bipolar forceps 501 to electrically connect the bipolar forceps 501 to the high-frequency cautery power supply unit 515. In the initial state, the trigger 517 of the operation portion 504 is pivoted to the direction indicated by the arrow a. In this state, the pair of elastic members 509*a* and 509*b* of the treatment portion 503 project from the inner sheath 507 to open the jaws 560*a* and 560*b*, as shown in FIG. 24B.

When the finger hook portions 517*a* and 517*b* of the trigger 517 are pulled to the grip 506 side against the spring force of the biasing members in the grip 506, the inner sheath 507 moves forward in the axial direction. As the inner sheath 507 moves forward, the elastic members 509*a* and 509*b* are relatively retracted into the inner sheath 507 to close the jaws 560*a* and 560*b*, as shown in FIG. 24A.

In this state, the insertion portion 502 of the bipolar forceps 501 is inserted into the body of a patient, and the treatment portion 503 at the distal end of the insertion portion 502 is placed near the vital tissue A to be treated in the body. When the trigger 517 is released, the trigger 517 returns to the home position by the spring force of the biasing member in the grip 506. The elastic members 509a and 509b relatively project from the inner sheath 507, and the jaws 560a and 560b are opened by the elastic restoring force of the elastic members 509a and 509b.

Figure 26A:
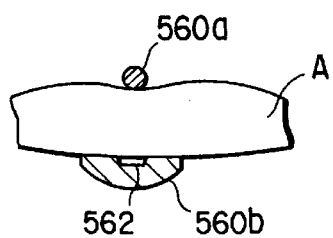
FIG. 26A is a sectional view of tissue coagulated by the high-frequency treatment tool shown in FIG. 24A.

After the vital tissue A is inserted between the opened jaws 560a and 560b, the finger hook portions 517a and 517b of the trigger 517 are pulled to the grip 506 side to move the inner sheath 507 forward in the axial direction. As the inner sheath 507 moves forward, the elastic members 509a and 509b are relatively retracted into the inner sheath 507 to close the jaws 560a and 560b. The vital tissue A is gripped between the pair of jaws 560a and 560b, as shown in FIG. 26A.

In this state, a high-frequency current is flowed from the high-frequency cautery power supply unit 515 to the connector receptacle 513 through the cable 514. A coagulation current is flowed across the jaws 560a and 560b to coagulate the vital tissue A.

Figure 26B:
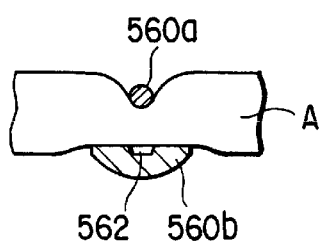
FIG. 26B is a sectional view of tissue incised by the high-frequency treatment tool shown in FIG. 24A.

Subsequently, when the finger hook portions 517a and 517b of the trigger 517 are further pulled to the grip 506 side, the jaws 560a and 560b are further closed, and an incision current is flowed across the jaws 560a and 560b, and the vital tissue A is incised by the pair of jaws 560a and 560b, as shown in FIG. 26B.

When coagulation and incision are complete, the trigger 517 is pivoted in the direction indicated by the arrow a. The inner sheath 507 moves backward, and the elastic members 509a and 509b are opened by the elastic restoring force. The jaws 560a and 560b are released from the vital tissue A.

Figure 27A:
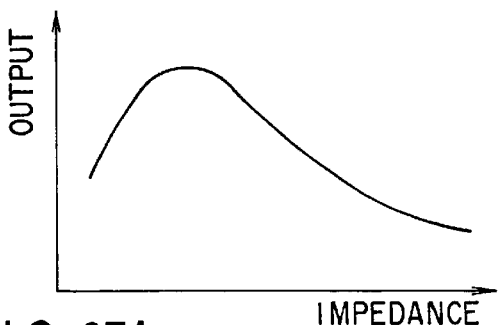
FIG. 27A is a graph showing the relationship between the output and the impedance upon coagulation.
Figure 27B:
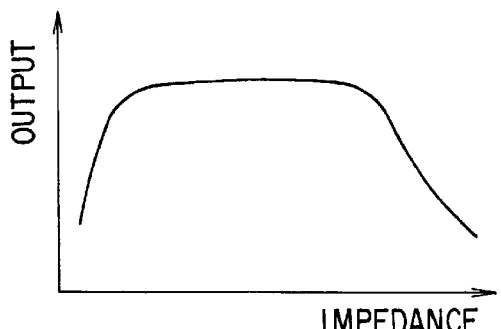
FIG. 27B is a graph showing the relationship between the output and the impedance upon incision.
Figure 27C:
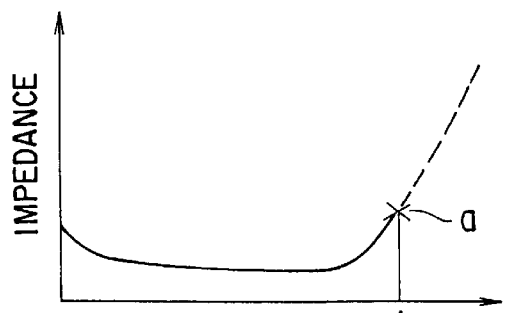
FIG. 27C is a graph showing changes in impedance at the time of supplying power to execute coagulation.

In this case, the incision current may be flowed upon determining that the vital tissue is completely coagulated on the basis of a change in impedance. More specifically, the coagulation current generally has load characteristics representing that when the impedance increases upon cautery, the output decreases, as shown in FIG. 27A. However, the incision current has a constant power output mode in which even when the impedance increases, the output does not decrease, as shown in FIG. 27B. As shown in FIG. 27C, in impedance control, when the generator determines that coagulation is complete at a point a when the impedance which has temporarily decreased increases again as the cautery time elapses, i.e., after coagulation is reliably performed, the incision current is flowed to incise the vital tissue A. That is, the coagulation current and the incision current can be automatically switched.

According to the findings in experiments conducted by the present inventors, for a bipolar structure, as in this embodiment, when the ratio of the projected areas of the jaws 560a and 560b (ratio of areas of portions in contact with the gripped tissue) is 1:10 to 1:2 (the upper jaw 560a has a diameter d of 0.5 to 2.5 mm, and the lower jaw 560b has a width w of 5 mm), the tissue can be satisfactorily coagulated/incised (when the tissue is gripped and coagulated by setting the coagulation output of a high-frequency oscillator at 30W, and then, incised by setting the incision output at 30W).

In the 17th embodiment shown in FIGS. 26A and 26B, the tissue is coagulated and incised by performing the gripping operation once. However, the tissue may be coagulated and incised by performing the gripping operation twice, as shown in FIGS. 28A to 28C. More specifically, the jaws 560a and 560b are closed by pulling the finger hook portions 517a and 517b of the trigger 517 to the grip 506 side. In this state, the insertion portion 502 of the bipolar forceps 501 is inserted into the body of a patient, and the treatment portion 503 at the distal end of the insertion portion 502 is guided near the vital tissue A to be treated in the body. When the trigger 517 is released, the trigger 517 returns to the home position by the spring force of the biasing member in the grip 506. The elastic members 509a and 509b relatively project from the inner sheath 507, and the jaws 560a and 560b are opened by the elastic restoring force of the elastic members 509a and 509b.

After the vital tissue A is inserted between the opened jaws 560a and 560b, the finger hook portions 517a and 517b of the trigger 517 are pulled to the grip 506 side to move the inner sheath 507 forward in the axial direction. As the inner sheath 507 moves forward, the elastic members 509a and 509b are relatively retracted into the inner sheath 507 to close the jaws 560a and 560b. The vital tissue A is gripped between the pair of jaws 560a and 560b, as shown in FIG. 28A.

In this state, a high-frequency current flows from the high-frequency cautery power supply unit 515 to the connector receptacle 513 through the cable 514. A coagulation current flows across the jaws 560a and 560b to coagulate the vital tissue A. In this case, a small gripping force is applied to the trigger 517 in accordance with a change in vital tissue A upon coagulation.

Subsequently, when the trigger 517 is released, the trigger 517 returns to the home position by the spring force of the biasing member in the grip 506. The elastic members 509a and 509b relatively project from the inner sheath 507, and the jaws 560a and 560b are opened by the elastic restoring force of the elastic members 509a and 509b. The jaws 560a and 560b are temporarily opened and separated from the vital tissue A, as shown in FIG. 28B.

The finger hook portions 517a and 517b of the trigger 517 are further pulled to the grip 506 side to close the jaws 560a and 560b until they come into contact with each other. At the same time, an incision current is flowed across the jaws 560a and 560b. The vital tissue A is incised by the pair of jaws 560a and 560b, as shown in FIG. 28C.

Upon completing coagulation and incision, the trigger 517 is pivoted in the direction indicated by the arrow a, the inner sheath 507 moves backward, and the elastic members 509a and 509b are opened by the elastic restoring force, so the jaws 560a and 560b are released from the vital tissue A.

FIGS. 29A to 30D show an 18th embodiment of the present invention. In this embodiment, of a pair of jaws 563a and 563b of a treatment portion 503, the upper jaw 563a is formed as a wire electrode having a triangular section. The lower jaw 563b has a flat shape. A recessed groove 564 opposing the jaw 563a is formed on the gripping surface, and serrate portions 565 are formed on both sides of the recessed groove 564. In this embodiment, since an electrode portion at the upper jaw 563a has a sharp edge portion, the ability of incising vital tissue A is excellent, and the operation force required for a trigger 517 can be reduced.

The effective electrode surface of the electrode formed of the upper jaw 563a is smaller than that of the electrode formed of the other jaw 563b. Accordingly, a current concentrates on the electrode of the upper jaw 563a, thereby enabling an efficient coagulation treatment and incision treatment. Further, this treatment tool can also perform the coagulation treatment and the incision treatment continuously while gripping vital tissue.

FIGS. 31A and 31B show a 19th embodiment of the present invention. The same reference numerals as in the 18th embodiment denote the same parts in the 19th embodiment, and a detailed description thereof will be omitted. In this embodiment, of a pair of jaws 566a and 566b of a treatment portion 503, the upper jaw 566a is formed into a knife shape having a triangular section to form a sharp portion 567 and has a hollow portion 568 at the central portion. The lower jaw 566b has a flat shape, and a serrate portion 565 is formed on the gripping surface. The arrangement of the remaining portions is the same as in the 18th embodiment. In this embodiment, since the upper jaw 566a has the sharp portion 567, the ability of incising vital tissue A is excellent, and the operation force required for a trigger 517 can be reduced.

FIGS. 32A and 32B show a 20th embodiment of the present invention. The same reference numerals as in the 18th embodiment denote the same parts in the 20th embodiment, and a detailed description thereof will be omitted. In this embodiment, of a pair of jaws 569a and 569b of a treatment portion 503, the upper jaw 569a is formed as an electrode having a prism-shaped section and a sharp portion 570 on one side. The lower jaw 569b has a flat shape, and a recessed groove 571 is formed in the gripping surface opposing the jaw 569a. The arrangement of the remaining portions is the same as in the 41st embodiment. In this embodiment, since the upper jaw 569a has the sharp portion 570, the ability of incising vital tissue A is excellent, and the operation force for a trigger 517 can be reduced.

For the pairs of jaws in the 18th to 20th embodiments, each of the upper jaw 563a, 566a, and 569b is formed as an electrode having a width of 1 to 2 mm to incise the vital tissue A simultaneously with coagulation, and each of the lower jaw 563b, 566b, and 569b having a flat shape has a tissue gripping surface width of about 5 mm and a ratio of 1:10 to 1:2, as in the 19th embodiment. The ratio of the effective electrode surface area of each electrode, which actually touches vital tissue A, to the entire surface area is 1:10 to 1:2.

FIGS. 33A to 34C show a 21st embodiment of the present invention. The same reference numerals as in the 17th embodiment denote the same parts in the 21st embodiment, and a detailed description thereof will be omitted.

Figure 33A:
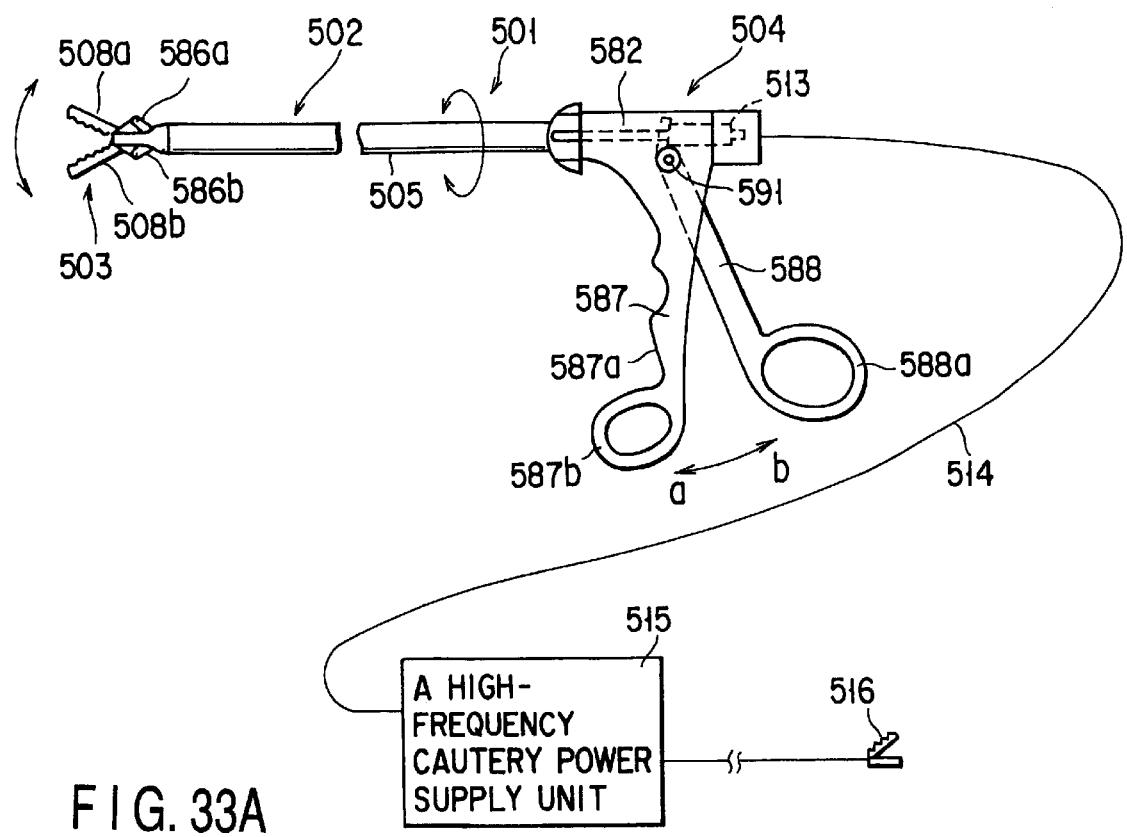
FIG. 33A is a view showing the overall arrangement of a high-frequency treatment tool according to a 21st embodiment of the present invention.
Figure 33B:
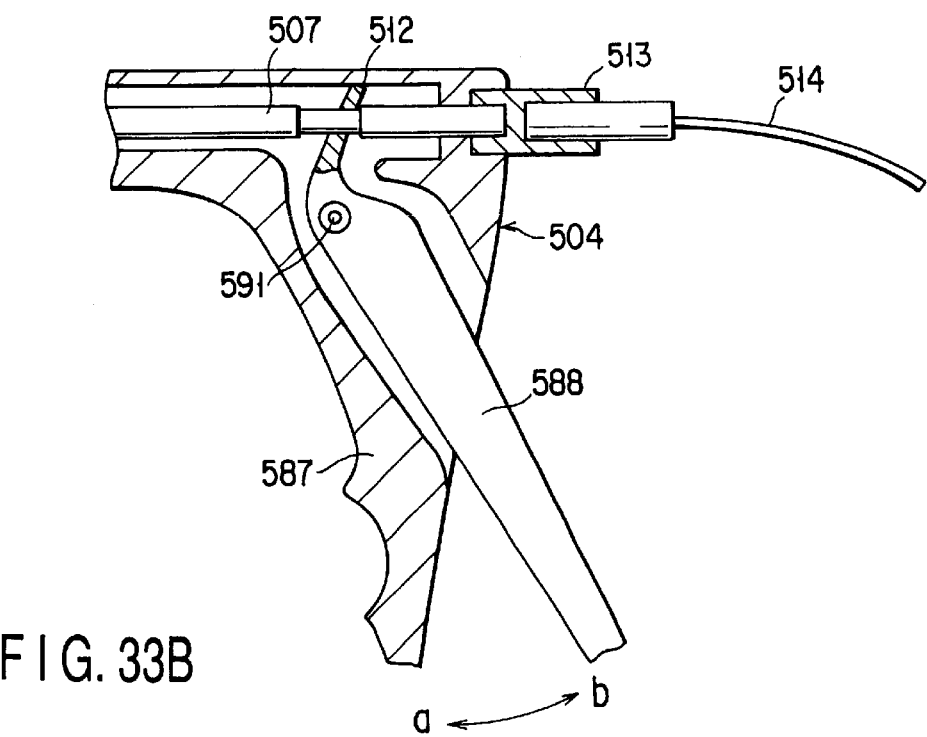
FIG. 33B is a sectional view of an operation portion of the high-frequency treatment tool shown in FIG. 33A.

FIGS. 33A and 33B are views showing the overall arrangement of a high-frequency treatment tool as an endoscopic operation tool. As shown in FIGS. 33A and 33B, a bipolar forceps 501 as a high-frequency treatment tool comprises a long insertion portion 502 to be inserted into the body cavity of a patient, a treatment portion 503 attached to the distal end portion of the insertion portion 502 to grip vital tissue and coagulate or incise it in the body cavity, to which power can be supplied, and an operation portion 504 coupled to the proximal end portion of the insertion portion 502.

Figure 34C:
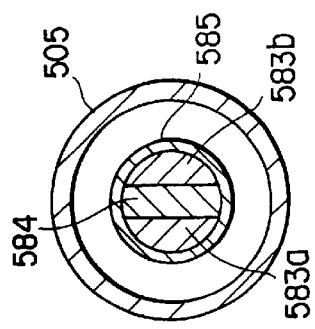
FIG. 34C is a sectional view taken along line 34C—34C in FIG. 34B.
Figure 34A:
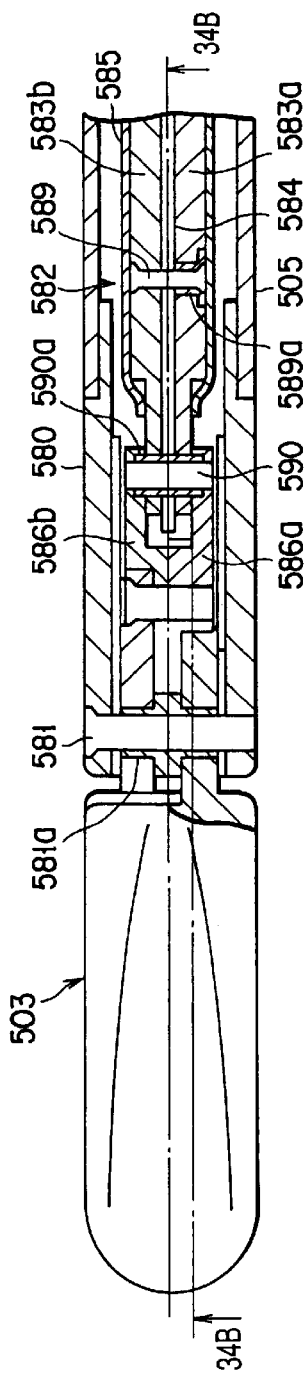
FIG. 34A is a cross-sectional view of the high-frequency treatment tool shown in FIG. 33A.
Figure 34B:
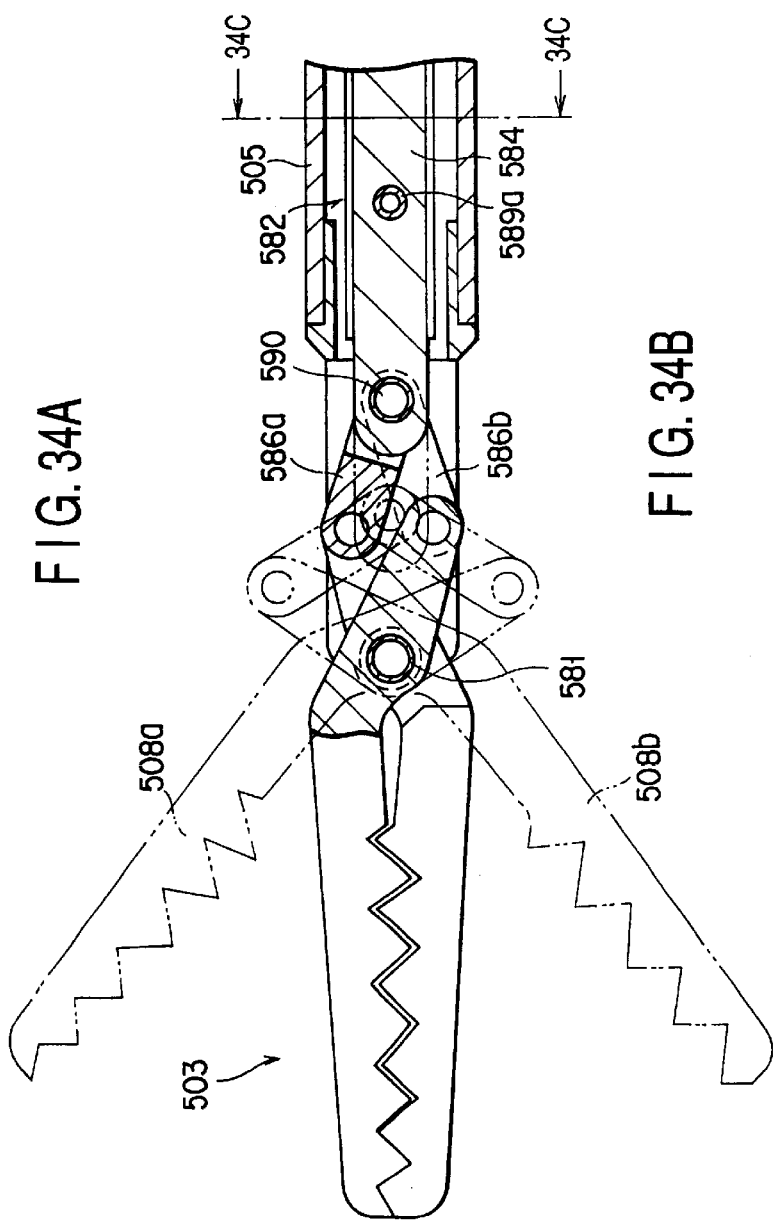
FIG. 34B is a sectional view taken along line 34B—34B in FIG. 33A.

The insertion portion 502 has a rotatable outer sheath 505. A tip cover 580 is attached to the distal end portion of the outer sheath 505, as shown in FIG. 34A. The tip cover 580 has a pin 581 for attaching the treatment portion 503. An operation rod 582 with its proximal end portion being inserted to a grip 506 of the operation portion 504 and its distal end portion being coupled to the treatment portion 503 is inserted into the outer sheath 505.

The operation rod 582 comprises two electrodes 583a and 583b having substantially semicircular sections and electrically insulated from each other, an insulating member 584 having a substantially rectangular section, and an insulating tube 585 covering these members. The electrodes 583a and 583b are coupled through a pin 589. The distal end portions of the electrodes 583a and 583b are coupled to links 586a and 586b through a pin 590. The links 586a and 586b are coupled to a pair of jaws 508a and 508b pivotally supported by the pin 581, respectively.

The pins 581, 589, and 590 are insulated by insulating members 581a, 589a, and 590a. A connector receptacle 513 is connected to a high-frequency cautery power supply unit 515 through a cable 514. The high-frequency cautery power supply unit 515 has a foot switch 516.

A fixed grip 587 of the operation portion 504 has a movable grip 588. The movable grip 588 is coupled to the upper end portion of the fixed grip 587 to pivot about a pivot pin 591. The upper end portion of the pivot fulcrum of the movable grip 588 is coupled to the proximal end portion of the operation rod 582. The movable grip 588 has a finger hook portion 588a on which the operator places the thumb. The fixed grip 587 has finger hook portions 587a and 587b on which the operator places the index and middle fingers, respectively. When the movable grip 588 is closed in a direction indicated by an arrow a, the operation rod 582 moves backward to close the jaws 508a and 508b through the links 586a and 586b. When the movable grip 588 is opened in a direction in indicated by an arrow b, the operation rod 582 moves forward to open the jaws 508a and 508b.

Figures 35A, 35B:
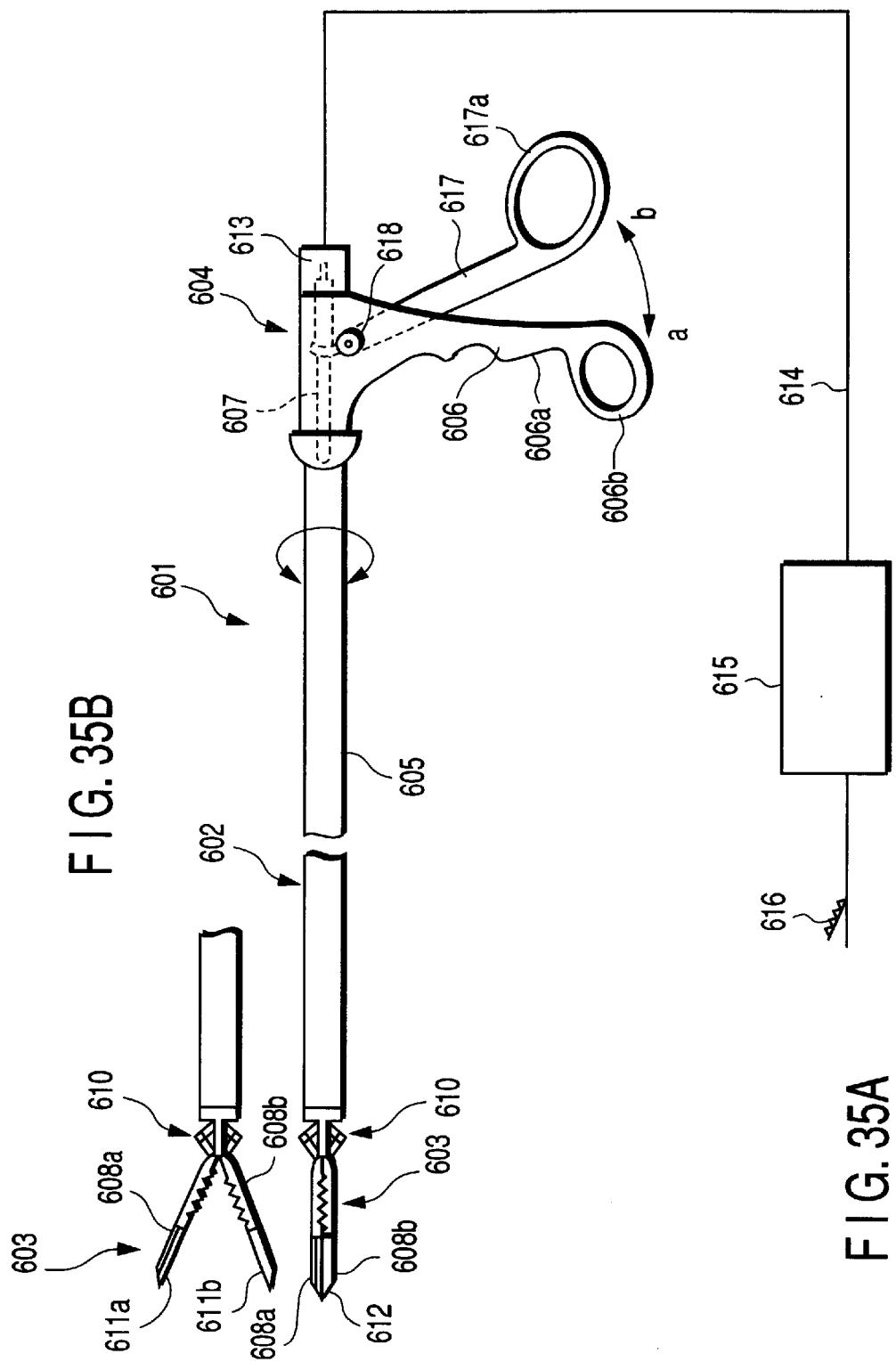
FIG. 35A is a view showing the overall arrangement of a high-frequency treatment tool according to a 22nd embodiment of the present invention.
FIG. 35B is a view useful in explaining a distal end portion of the high-frequency treatment tool of the 22nd embodiment in the open state.
Figure 36:
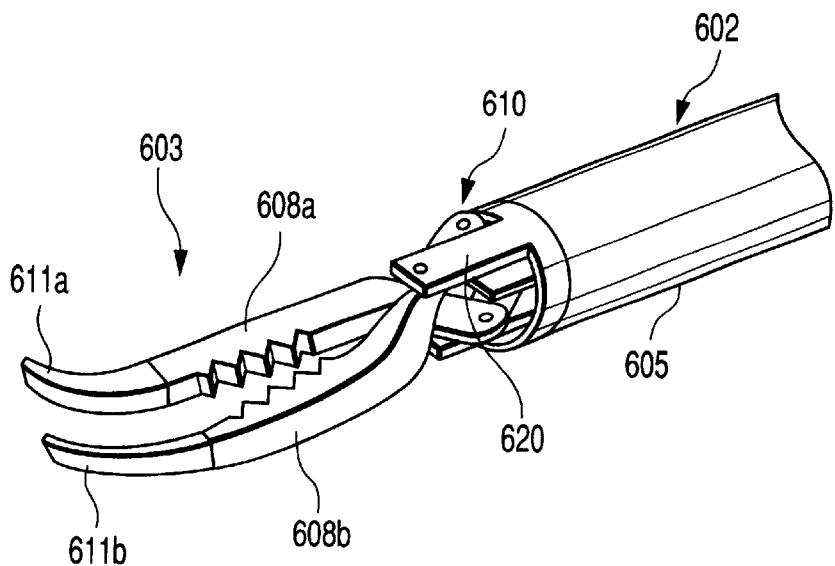
FIG. 36 is a perspective view showing distal end portion of the high-frequency treatment tool of the 22nd embodiment.

FIGS. 35A–39B illustrate a high-frequency treatment tool according to a 22nd embodiment of the present invention. As shown in FIG. 35A, the high-frequency treatment tool of this embodiment is formed as a bipolar forceps 601. The bipolar forceps 601 comprises a long insertion portion 602 to be inserted into the body cavity of a patient, a treatment portion 603 attached to the distal end portion of the insertion portion 602 to grip vital tissue and coagulate or incise it in the body cavity, and an operation portion 604 coupled to the proximal end portion of the insertion portion 602. A high-frequency current is supplied to the treatment portion 603 via a conductive member, thereby enabling the treatment portion 603 to coagulate/incise the gripped vital tissue.

The insertion portion 602 has a rotatable outer sheath 605, and a rod 607 is axially movably inserted in the sheath 605. A pair of jaws 608a and 608b constituting the treatment portion 603 are coupled to the distal end of the rod 607 via a link mechanism 10. The jaws 608a and 608b function as gripping members for gripping vital tissue between gripping surfaces thereof opposed to each other, and are provided with bipolar electrodes having a function for flowing a high frequency current to the gripped tissue.

FIGS. 36–38B are enlarged views of a distal end portion of the insertion portion 602 and the treatment portion 603 incorporated in the bipolar forceps 601 shown in FIG. 35A. As shown, in particular, in FIGS. 37 and 38C, each of the jaws 608a and 608b has a slim body tapered from its proximal end to its distal end. Proximal end portions of the jaws 608a and 608b are pivotally attached to a pair of support arms 602 by means of a common support pin 625.

A link mechanism 610 has a pair of links 621 and 622 rotatably coupled to the distal end of a rod 607 via a support pin 629. The first link 621 is rotatably coupled to a proximal extended portion of the jaw 608b via a support pin 623. The second link 622 is rotatably coupled to a proximal extended portion of the jaw 608a via a support pin 624. Accordingly, when the rod 607 has been shifted by the link mechanism 610 along its axis, the jaws 608a and 608b pivot on the pin 625, whereby the distal ends of the jaws 608a and 608b pivot to their open positions. In other words, the link mechanism constitutes an operation unit operated by a handle, described later, for opening and closing the jaws 608a and 608b of the treatment portion 603.

Figures 38A, 38B, 38C:
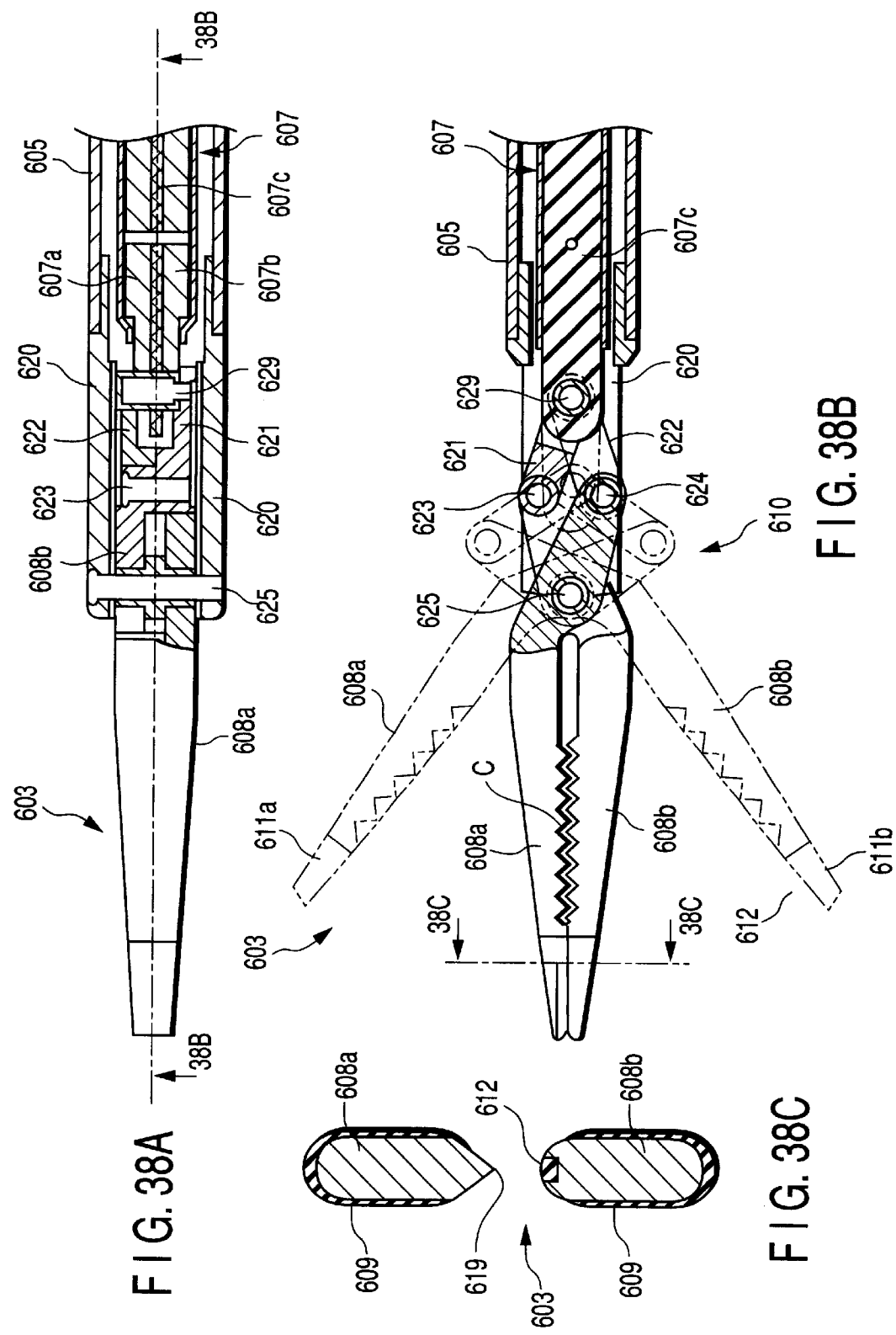
FIG. 38A is a sectional view showing a treatment portion of the high-frequency treatment tool of the 22nd embodiment in the closed state.
FIG. 38B is a sectional view taken along line 38B—38B in FIG. 38A, illustrating, by the imaginary lines, the open state of the treatment portion of the high-frequency treatment tool of the 22nd embodiment.
FIG. 38C is a sectional view taken along line 38C—38C in FIG. 38B.

As shown in FIG. 38A, respective bushes made of, for example, an electrically insulated material are fitted on the support pin 625 connecting the jaws 608a and 608b and on the support pin 629 connecting the first and second links 621 and 622. This structure prevents the electrodes from short circuiting through the support pins 625 and 629.

Figure 37:
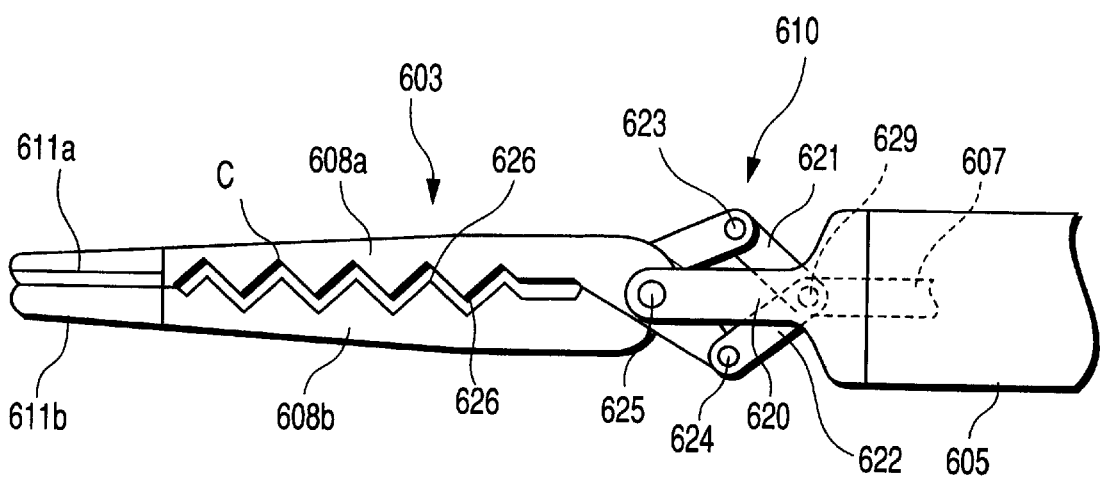
FIG. 37 is an enlarged side view showing the distal end portion of the high-frequency treatment tool shown in FIG. 35A.

Serrate portions 626 as coagulation portions are formed on the gripping surfaces of the jaws 608a and 608b, which are situated at the proximal end side of the jaws. The serrate portions 626 are situated in proximal areas of the jaws 608a and 608b, and their gripping surfaces are formed wide. Further, as shown in FIG. 37, when distal end portions 611a and 611b of the jaws 608a and 608b have been pivoted to approach each other and close the treatment portion 603, the projections and depressions of the serrate portions 626 opposed to each other are engaged, thereby reliably gripping vital tissue.

As shown in FIG. 38C, a narrow strip-shaped insulation portion 612 is formed in the gripping surface of the distal end portion 611b of the jaw 608b such that it extends in the insertion direction of the insertion portion 602. An incision portion (electrode portion) 619 is formed in the area of the gripping surface of the distal end portion 611a of the jaw 608a, which corresponds to the insulation portion 612. The incision portion 612 is in the form of a projection having a triangular cross section, i.e. in the form of sort of a blade. The distal end of the incision portion 619 extends in the longitudinal direction of the jaw 608a and in the insertion direction of the insertion portion 602.

The pair of jaws 608a and 608b constitute, in their proximal areas, a coagulation gripping area section having the serrate portions 626, and also constitute, in their distal areas, an incision gripping area section having the incision portion 619 and the insulation portion 612 opposed thereto. In the incision gripping area section, the jaw 608a includes a blade and the incision portion 619 attached thereto as a cutting edge. Specifically, as shown in FIG. 38C, the blade member including the incision portion 619 has a transverse cross section of a narrow width, and the back portion of the blade member is formed arcuate. The blade member is in the form of a thin plate that has a width substantially constant from the back portion to a proximal end of the incision portion 619 as the cutting edge. In other words, the blade member incorporated in the jaw 608a with the incision portion 619 has a thin thickness in the direction perpendicular to the pivoting direction of the jaw. The incision portion 619 is tapered to its tip.

In the distal end portions of the jaws 608a and 608b, the effective electrode surface of the electrode portion of the jaw 608a differs from that of the electrode portion of the jaw 608b. That is, the former is smaller than the latter.

In this embodiment, the blade member having the insulation portion 612 and included in the jaw 608b is formed of a thin plate member, which is thin in a direction perpendicular to the direction of pivoting. However, the cross section of the gripping end surface of the jaw 608b having the insulation portion 612 is arcuate in the same manner as the back portion of the blade member. In the incision gripping area section, when the incision portion 619 of the upper jaw 608a is in contact with the insulation portion 612 of the lower jaw 608b, a predetermined clearance C is defined between the gripping surfaces in the coagulation gripping area section, i.e. between the serrate portions 626.

A jaw outer peripheral insulation portion 609 is provided at the peripheral surface of each jaw 608a or 608b except for the gripping surface. The jaw outer peripheral insulation portion 609 is provided for increasing the intensity of a current supplied to the gripping surface, and also for reducing the amount of an unnecessary current supplied to the portions of vital tissue other than a target portion. Both the insulation portion 612 and the jaw outer peripheral insulation portion 609 are electrically insulated. These portions can be formed by providing to-be-insulated portions of each jaw 608a or 608b with an electrically insulated material such as a resin. Alternatively, these portions can be formed by providing the to-be-insulated portions of each jaw 608a or 608b with electrically insulated coating.

As described above, in this embodiment, when the treatment portion 603 is completely closed, the incision portion 619 of the jaw 608a is in contact with the insulation portion 612 of the jaw 608b. Accordingly, the predetermined clearance C is defined between the gripping surfaces of the jaws 608a and 608b, i.e. between the serrate portions 626, but not between the incision portion 619 and the insulation portion 612. Therefore, while a high-frequency current is being supplied to the jaws 608a and 608b that grip vital tissue therebetween, their conductive portions do not touch each other (the jaws 608a and 608b do not short-circuit). Further, the serrate portions 626 do not come into contact, which secures, at the final stage, the engagement of the incision portion 619 of the jaw 608a with the insulation section 612 of the jaw 608b in the incision gripping area. As a result, vital tissue can be reliably incised in the incision gripping area section.

A conductive member electrically connected to the jaws 608a and 608b extends to the operation portion 604 through the sheath 605 shown in FIG. 22, and is connected to a connector-receiving portion 613 provided in the operation portion 604. Thus, a current supply device is constructed for supplying the electrode portions of the jaws 608a and 608b with a high-frequency treatment current to be flowed to vital tissue.

A cable 614 extending from a high-frequency cautery power supply unit 615 is connected to the connector-receiving portion 613. A foot switch 616 for turning on/off the high-frequency cautery power supply unit 615 is attached thereto.

As shown in FIG. 35A, the operation portion 604 has a grip 606. The grip 606 includes finger hook portions 606a and 606b for hooking the index and middle fingers of the operator, respectively. The grip 606 further includes a trigger (handle) 617 as a forceps operation unit for enabling the fingers to open and close the treatment portion 603, i.e. the jaws 608a and 608b. The trigger 617 is coupled to an upper end portion of the grip 606 such that it can freely pivot about a pivot pin 618. The trigger 617 is coupled to a proximal end portion of the rod 607, and enables the operator to move the rod 607 forward and backward. The trigger 617 has a finger hook portion 617a at its distal end for hooking the thumb of the operator.

A description will now be given of the case of coagulating vital tissue using the bipolar forceps 601 constructed as above. First, the cable 614 is connected to the connector-receiving portion 613 of the bipolar forceps 601, thereby electrically connecting the bipolar forceps 601 to the high-frequency cautery power supply unit 615. Subsequently, the trigger 617 of the operation portion 604 is pivoted in the direction indicated by arrow a in FIG. 35A, thereby retreating the rod 607 toward the proximal end thereof and closing the jaws 608a and 608b of the treatment portion 603 via the link mechanism 610. With the treatment portion 603 closed, the insertion portion 602 of the bipolar forceps 601 is inserted, while performing observation using the endoscope, into the body cavity of a patient to thereby guide the treatment portion 603 of the insertion portion 602 to a position near tissue to be treated.

After positioning the treatment portion 603 near the tissue to be treated, the rod 607 is moved forward by pivoting the trigger 617 in the direction indicated by arrow b in FIG. 35A, thereby causing the link mechanism 610 to open the jaws 608a and 608b (the treatment portion 603). The target tissue is gripped between the opened jaws 608a and 608b. At this time, even if the tissue is thin, the conductive portions of the jaws 608a and 608b, through which a high-frequency current flows, are prevented from coming into contact with each other, thereby avoiding short circuit therebetween. This is because when the treatment portion 603 is completely closed, the incision portion 619 of the jaw 608a located near the proximal end thereof is in contact with the insulation portion 612 of the jaw 608b, and therefore the jaws 608a and 608b are electrically insulated from each other. In this state, the predetermined clearance C is defined between the serrate portions 626 provided at proximal gripping surfaces of the jaws 608a and 608b, which secures electrical insulation between the jaws.

In this state, the cable 614 connected to the high-frequency cautery power supply unit 615 is connected to the connector-receiving portion 613, thereby supplying a coagulation or incision current of a controlled predetermined frequency between the jaws 608a and 608b. As a result, the vital tissue gripped by the jaws is coagulated or incised.

Coagulation of vital tissue is executed not only in the case of coagulating the vital tissue while gripping it in the coagulation gripping area section, and incising the tissue while gripping it in the incision gripping area section. The vital tissue can be coagulated and incised by gripping it in the incision gripping area section. Further, where vital tissue is gripped by the distal end portions of the jaws 608a and 608b, only coagulation can be executed. In particular, a treatment executed at the distal end portions of the jaws 608a and 608b is suitable for coagulating a portion from which a small amount of blood is bleeding, or a very small portion.

When coagulating a large size of tissue including, for example, a blood vessel, the tissue is reliably gripped between proximal gripping areas of the jaws 608a and 608b, whereby a current is supplied thereto to coagulate it. Thus, the distal gripping areas and the proximal gripping areas of the jaws 608a and 608b can be used for different treatments or different states of target tissue.

Figure 39A:
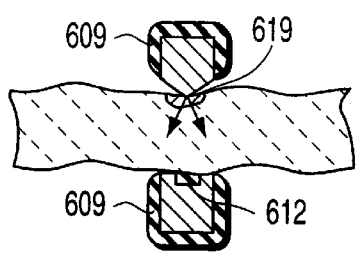
FIG. 39A is a view illustrating a state in which vital tissue is being coagulated/incised by the high-frequency treatment tool shown in FIG. 35A.
Figure 39B:
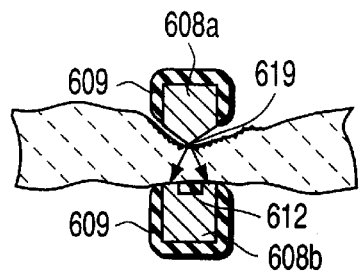
FIG. 39B is a view illustrating another state in which vital tissue is being coagulated/incised by the high-frequency treatment tool shown in FIG. 35A.

In addition, incision including coagulation can be performed by gripping vital tissue between the distal end portions of the jaws 608a and 608b and supplying an incision current thereto. FIGS. 39A and 39B show states of coagulation, in which a coagulation function is applied to the distal end portions of the jaws 608a and 608b, thereby incising vital tissue. In this case, there is a difference between the effective electrode surfaces of the jaws 608a and 608b, which are to be brought into contact with the vital tissue when gripping it. More specifically, the effective electrode surface of the jaw 608a is smaller than that of the other jaw 608b. Accordingly, a current concentrates on the jaw 608a having a smaller effective electrode surface. As a result, local incision is performed in a portion as well as local coagulation as shown in FIGS. 39A and 39B. Thus, coagulation and incision are simultaneously executed. This means that a coagulation treatment and an incision treatment can be executed continuously and efficiently with vital tissue gripped.

Figure 40A:
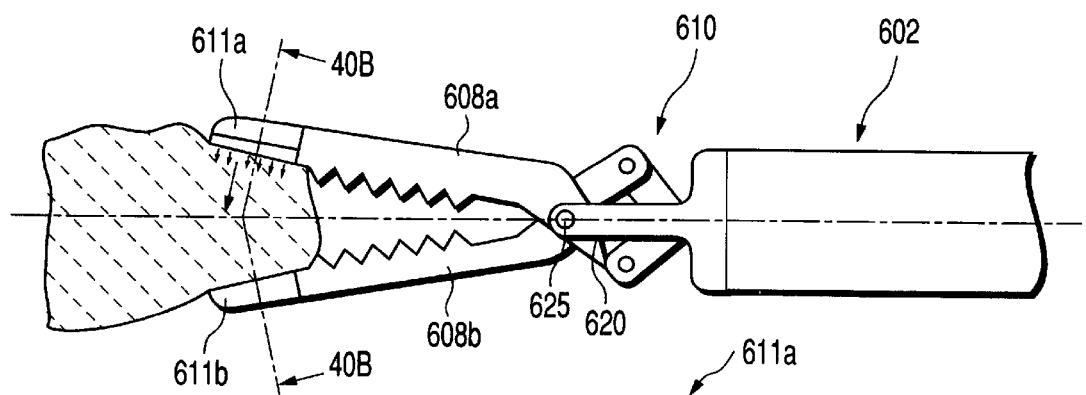
FIG. 40A is a view illustrating a state in which vital tissue is incised by the high-frequency treatment tool shown in FIGS. 35A and 35B.
Figure 40B:
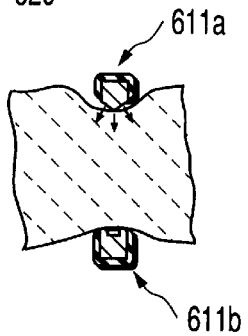
FIG. 40B is a sectional view taken along line 40B—40B in FIG. 40A.

Furthermore, as shown in FIGS. 40A and 40B, simple incision can be also performed by starting the supply of an incision current to the jaws 608a and 608b when the jaws are open, and closing the distal ends of the jaws 608a and 608b with the supply of the current maintained.

The above-described bipolar forceps 601 can perform coagulation of tissue from which a small amount of blood is bleeding, coagulation of a large size of tissue, and incision including coagulation using the distal end portions of the jaws 608a and 608b. Moreover, a treatment such as incision, gripping, or peeling, etc. of a very small portion can be executed very simply without exchanging the forceps with another one.

Also, since the effective electrode surface of the jaw 608a is smaller than that of the other jaw 608b, a current concentrates on the jaw 608a having a smaller effective electrode surface, which is to be brought into contact with vital tissue when gripping it. As a result, both a coagulation treatment and an incision treatment can be executed efficiently. Further, a local and continuous coagulation treatment and incision treatment can be executed, while gripping the tissue.

As described above, the bipolar forceps 601 of this embodiment itself can perform various types of treatments such as coagulation, incision, gripping and peeling, etc. of vital tissue. Accordingly, it is not necessary to exchange the forceps in accordance with the type of treatment while using it. This means that the forceps 601 is a very handy tool to a doctor, and therefore, the time required for an operation can be shortened, for example.

Furthermore, the area of the blade member of the jaw 608a, in which the incision portion 619 is provided, has a transversal cross section of a narrow width in the direction perpendicular to the pivoting direction of the jaw, as is shown in FIG. 38C. If the blade portion is thick, the blade portion other than the incision portion 619 grips the tissue surrounding target tissue to be incised, and hence it is difficult to incise the target tissue. In the embodiment, however, the blade portion including the incision portion 619 is thin, local and smooth incision of tissue can be executed using only the incision portion 619. Since, in particular, the incision portion 619 is in the form of a sharp blade, a high-frequency current concentrates on the sharp edge, thereby enabling efficient incision using the high-frequency current. Local coagulation/incision can be performed even on a fine portion of the body.

If the blade member having the incision portion 619 is thick, i.e. has a wide width, the portion of the blade member other than the incision portion 619 might hold vital tissue as well as the incision portion, and hence the incision portion 619 may not efficiently incise or coagulate the vital tissue. The higher the pivoting speed of the jaw 608a, the higher the possibility of occurrence of this phenomenon. However, in the embodiment, the phenomenon does not occur even when the pivoting speed of the jaw is high.

Further, in the embodiment, tissue does not touch the blade member of the jaw 608a other than the incision portion 619, and the left and right portions of tissue incised by the incision portion 619 are laterally parted by the jaw 608a in a smooth manner. Accordingly, the forward movement of the incision portion 619 of the jaw 608a is not interrupted. Only the incision portion 619 of the jaw 608a can smoothly cut into tissue to be incised or coagulated. As a result, the incision portion 619 can incise or coagulate only a desired portion. Moreover, the jaw 608a has a shape that does not mechanically interfere with the left and right portions of incised or coagulated tissue. Therefore, the tissue to be incised or coagulated by the incision portion 619 of the jaw 608a is not unnecessarily moved by the jaw 608a.

Figure 41A:
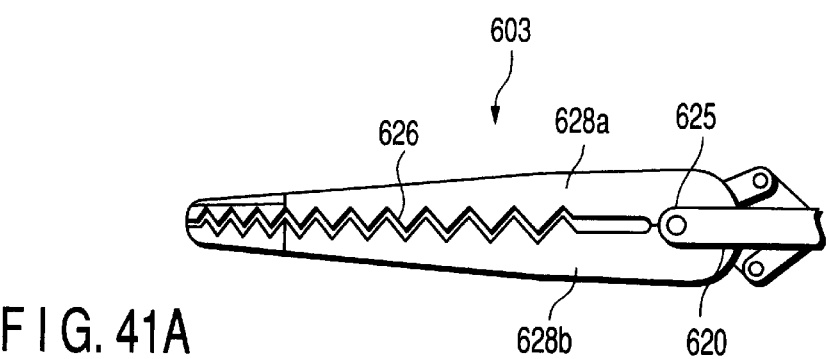
FIG. 41A is a side view showing a treatment portion incorporated in a modification of the high-frequency treatment tool shown in FIG. 35A.
Figure 41B:
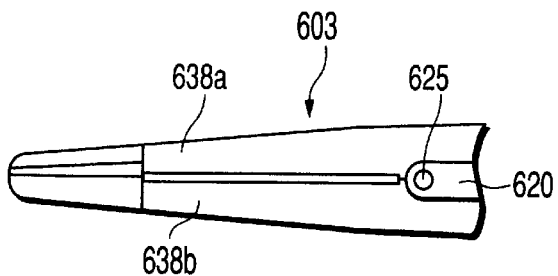
FIG. 41B is a side view showing a treatment portion incorporated in another modification of the high-frequency treatment tool shown in FIG. 35A.

FIGS. 41A and 41B illustrate two modifications of the treatment portion 603. A pair of jaws 628a and 628b employed in the modification shown in FIG. 41A each include a serrate portion 626 provided at the entire gripping surface, i.e. even at the incision portion 619. On the other hand, a pair of jaws 638a and 638b employed in the modification shown in FIG. 41B have no serrate portion over the entire gripping surfaces. The other structures of the jaws 628a, 628b, 638a and 683b are similar to those of the jaws 608a and 608b.

The forceps having the jaws 628a and 628b shown in FIG. 41A has a higher gripping performance, while the forceps having the jaws 638a and 638b shown in FIG. 41B has a higher incision performance. The other advantage is similar to that of the above-described 22nd embodiment.

Figure 43A:
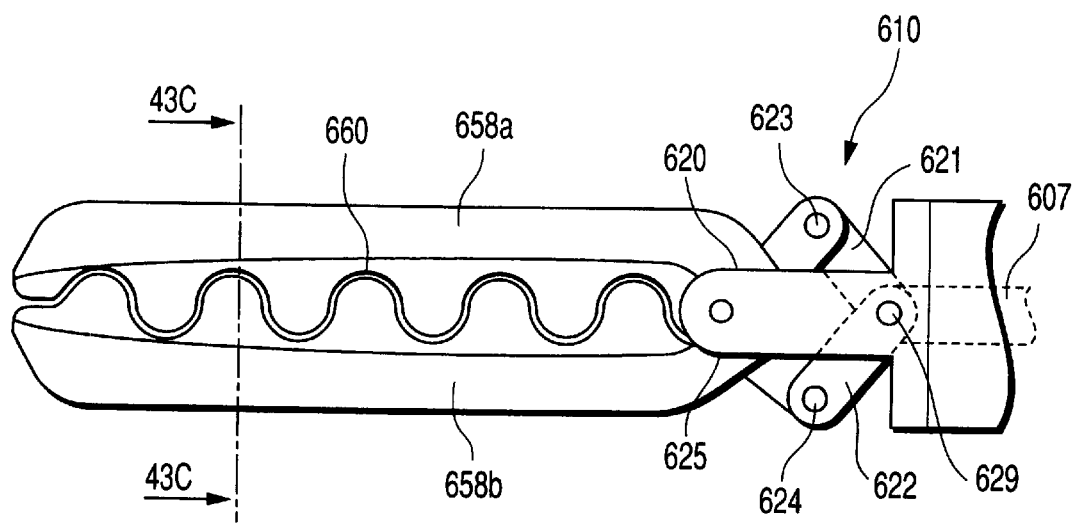
FIG. 43A is a view showing a distal end portion of the high-frequency treatment tool of the 23rd embodiment.
Figure 43B:
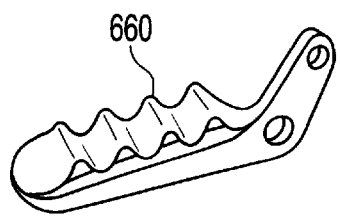
FIG. 43B is a perspective view showing a jaw incorporated in the high-frequency treatment tool of the 23rd embodiment.
Figure 43C:
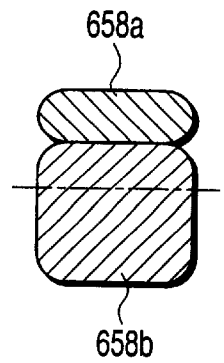
FIG. 43C is a sectional view taken along line 43C—43C in FIG. 43A.
Figure 44:
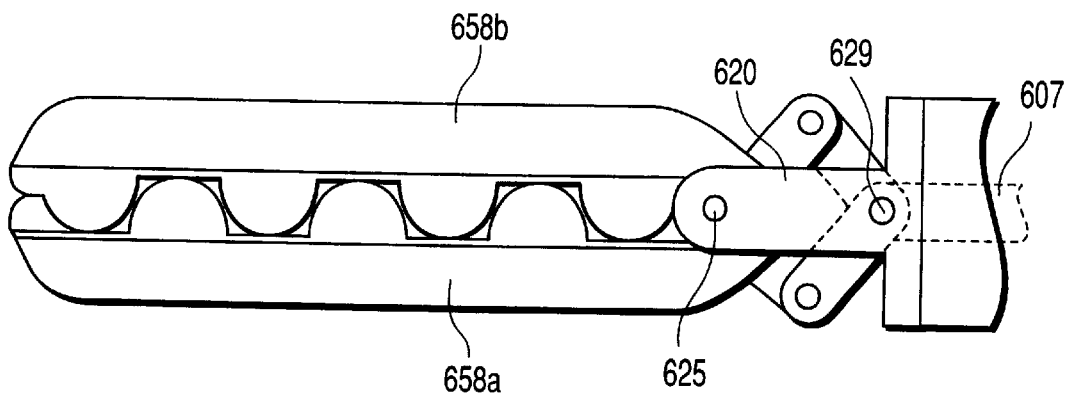
FIG. 44 is a view illustrating a modification of the treatment portion of the high-frequency treatment tool of the 23rd embodiment.
Figure 45:
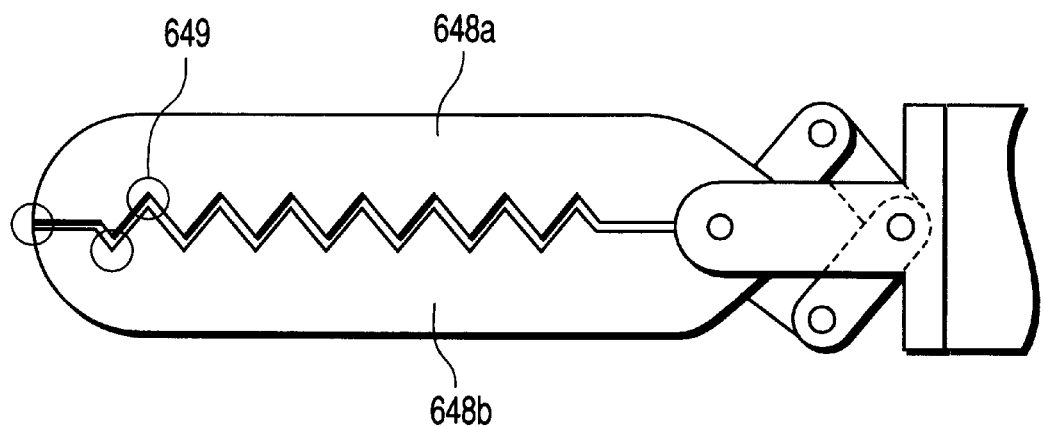
FIG. 45 is an enlarged view showing a distal end portion of a conventional high-frequency treatment tool.
Figure 46:
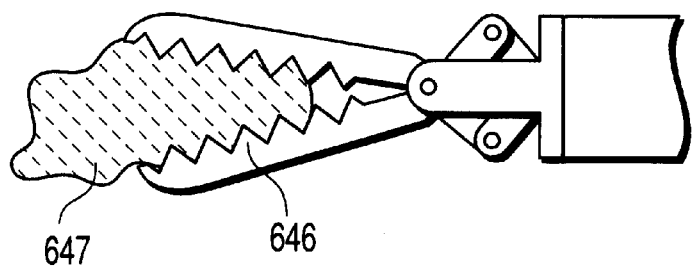
FIG. 46 is a view useful in explaining a state in which tissue is coagulated by the conventional high-frequency treatment tool.

FIGS. 42A–44 illustrate a high-frequency treatment tool according to a 23rd embodiment of the present invention. This embodiment is provided for preventing vital tissue from burning to or adhering to the jaws, even if a high frequency current is applied to the vital tissue where it is firmly gripped. To sufficiently coagulate vital tissue, it is necessary to apply a high frequency current to the vital tissue while firmly gripping it. To this end, in the prior art, a serrate portion 649 or projections are provided at the gripping surface of each jaw 648a or 648b as shown in FIGS. 45 and 46. EP 0584787 describes a forceps having jaws provided with serrate portions at gripping surfaces thereof, which can reliably grip vital tissue without damaging the tissue when, for example, pulling it, even if the tissue includes a blood vessel.

However, when vital tissue 647 is gripped between the jaws 648a and 648b having such serrate portions 649, it may be easily ground down. Moreover, if a high frequency current is applied to the tissue in this state, the intensity of the current is partially increased because of the sharpness of the serrate portions 649. As a result, the tissue 647 may burn to or adhere to the gripping surfaces 646 of the jaws 648a and 648b.

The forceps of EP 0584787 is intended so as not to damage tissue when gripping or pulling it, but not intended to prevent tissue from burning or adhering thereto when a high frequency current is flowed.

As in the 22nd embodiment, the bipolar forceps 601 as the high-frequency treatment tool of this embodiment comprises a long insertion portion 602 to be inserted into the body cavity of a patient, a treatment portion 603 attached to a distal end portion of the insertion portion 602 to grip vital tissue and coagulate or incise it in the body cavity, and an operation portion 604 coupled to a proximal end portion of the insertion portion 602. A high-frequency current is supplied to the treatment portion 603 via a conductive member, thereby enabling the treatment portion 603 to coagulate/incise the gripped vital tissue.

Further, as in the 22nd embodiment, the insertion portion 602 has a rotatable outer sheath 605, and a rod 607 is axially movably inserted in the sheath 605. A pair of jaws 658a and 658b constituting the treatment portion 603 are coupled to the distal end of the rod 607 via a link mechanism 610. The jaws 658a and 658b function as gripping members for gripping vital tissue between their gripping surfaces opposed to each other, and also function as electrodes for flowing a high frequency current to the gripped vital tissue.

As shown in detail in FIG. 43A, the link mechanism 610 has a pair of links 621 and 622 rotatably coupled to the distal end of the rod 607 via a support pin 629, as in the 22nd embodiment. The links 621 and 622 are rotatably coupled to proximal extended portions of the jaws 658b and 658a via support pins 623 and 624, respectively. Accordingly, when the rod 607 has been shifted by the link mechanism 610 along its axis, the jaws 658a and 658b pivot on the pin 625, thereby opening the treatment portion 603.

Further, as in the 22nd embodiment, respective bushes made of, for example, an electrically insulated material are fitted on the support pin 625 connecting the jaws 658a and 658b to an arm portion 620 and on the support pin 629 connecting the links 621 and 622. This structure prevents the electrodes from short circuiting through the support pins 625 and 629.

As shown in FIGS. 43A and 43B, the jaws 658a and 658b each have a tissue gripping surface 660 provided with a plurality of projections for reliably gripping vital tissue. These projections do not have sharp edges so as to prevent vital tissue from burning to or adhering to the jaws. More specifically, the tissue gripping surfaces 660 of the jaws 658a and 658b, which are to be brought into contact with vital tissue, have a plurality of R-shaped, i.e. smoothly curved, projections. The grooves defined between adjacent projections may have smoothly curved bottom as shown in FIGS. 43A and 43B, or flat bottoms as shown in FIG. 44. In any case, it is preferable that the projections are engaged with the grooves when the treatment portion 603 is closed.

As shown in FIG. 42A, a conductive member, which is electrically connected to the jaws 658a and 658b, extends through the sheath 605 and is connected to a connector-receiving portion 613 provided in the operation portion 604, as in the 22nd embodiment. A cable 614 extending from a high-frequency cautery power supply unit 615 is connected to the connector-receiving portion 613. A foot switch 616 for turning on/off the high-frequency cautery power supply unit 615 is attached thereto. The operation portion 604 has a grip 606. The grip 606 includes finger hook portions 606a and 606b for hooking the index and middle fingers of the operator, respectively. The grip 606 further includes a trigger 617 as forceps operation means. The trigger 617 is coupled to an upper end portion of the grip 606 such that it can freely pivot about a pivot pin 618. The trigger 617 is coupled to a proximal end portion of the rod 607, and has a finger hook portion 617a at its distal end for hooking the thumb of the operator.

A description will now be given of the case of coagulating vital tissue using the bipolar forceps 601 according to this embodiment. First, the cable 614 is connected to the connector-receiving portion 613 of the bipolar forceps 601, thereby electrically connecting the bipolar forceps 601 to the high-frequency cautery power supply unit 615. Subsequently, the trigger 617 of the operation portion 604 is pivoted in the direction indicated by arrow a in FIG. 42A, thereby retreating the rod 607 toward the proximal end thereof and closing the jaws 658a and 658b (the treatment portion 603) via the link mechanism 610. With the treatment portion 603 closed, the insertion portion 602 of the bipolar forceps 601 is inserted into the body cavity of a patient to thereby guide the treatment portion 603 of the insertion portion 602 to a position near tissue to be treated.

After positioning the treatment portion 603 near the tissue to be treated, the rod 607 is moved forward by pivoting the trigger 617 in the direction indicated by arrow b in FIG. 42A, thereby causing the link mechanism 610 to open the jaws 658a and 658b (the treatment portion 603). The target tissue is gripped between the opened jaws 658a and 658b.

In this state, a high frequency current is flowed from the high-frequency cautery power supply unit 615 to the connector-receiving portion 613 via the cable 614, thereby supplying a coagulation or incision current of a predetermined frequency between the jaws 658a and 658b. As a result, the vital tissue gripped by the jaws is coagulated or incised.

In the prior art shown in FIGS. 45 and 46, when a current is flowed to the gripped vital tissue 647, the intensity of the current is higher at the serrate portion 649. As a result, cautery is performed at the serrate portion and hence it is very possible that tissue may burn to or adhere to the serrate portion. On the other hand, in this embodiment, the tissue gripping surfaces 660 of the jaws 658a and 658b have smooth projections with no edges. Therefore, the intensity of the current is prevented from becoming locally higher. Thus, the high-frequency treatment tool of this embodiment can coagulate vital tissue while suppressing the burning or adhesion of the tissue to the jaws 658a and 658b. Further, stopper means (not shown) may be provided so that the gripping surfaces of the jaws 658a and 658b can be stopped in a position in which they are out of contact with vital tissue.

FIGS. 47A to 53 illustrate a high-frequency treatment tool according to a 24th embodiment of the present invention. The high-frequency treatment tool of this embodiment is constructed as a bipolar forceps 601 as the above-described embodiment, and comprises a long insertion portion 602 to be inserted into the body cavity of a patient, a treatment portion 603 attached to a distal end portion of the insertion portion 602 to grip vital tissue and coagulate or incise it in the body cavity, and an operation portion 604 coupled to a proximal end portion of the insertion portion 602.

The treatment portion 603 is coupled to the distal end of a rod (shaft) 607 that incorporates a conductive member. These elements are integrated into a treatment tool unit 665. The insertion portion 602 has a rotatable sheath 605 in which the rod 607 is axially movably inserted. A rotatable operation knob 664 is fixed to the proximal end of the sheath 605. The insertion portion 602 and the treatment tool unit 665 coupled thereto can be simultaneously rotated by operating the rotatable operation knob 664.

A pair of jaws 608a and 608b constituting the treatment portion 603 are coupled to the distal end of the rod 607 via a link mechanism 610. The jaws 608a and 608b function as gripping members for gripping vital tissue between their gripping surfaces opposed to each other, and also function as electrodes for flowing a high frequency current to the gripped vital tissue.

FIGS. 48A and 48B are enlarged views illustrating a distal end portion of the insertion portion 602 and the treatment portion 603, which are incorporated in the bipolar forceps 601, and also illustrating a current supply structure for supplying a treatment high-frequency current to a pair of electrode portions opposed to each other. The jaws 608a and 608b are coupled to a pair of support arms 620 projecting from the distal end of the sheath 5, and to the distal end of the rod 607. As shown in FIG. 48C, only a proximal end portion 666 of the upper jaw 608a is directly pivotably supported by the pair of support arms 620 via a pivot pin 667. Further, as shown in FIG. 48D, a proximal end portion 668 of the lower jaw 608b is divided into two portions, between which the proximal end portion 666 of the upper jaw 608a is sandwiched. Both the proximal end portions 666 and 668 are pivotably connected to each other via a pivot pin 669 extending therebetween. An electrically insulated protection tube 670 is fitted on the pivot pin 669, and further fitted in the proximal end portion 666 of the upper jaw 608a, thereby electrically insulating the upper jaw 608a from the lower jaw 608b.

As shown in FIG. 48E, a front end portion of a connection member 671 coupled to the distal end of the rod 607 is fitted between the divided proximal end portions 668 of the lower jaw 608b, and both the members are pivotably connected via a pivot pin 672. As shown in FIG. 48B, a distal end portion of a shaft 675, which constitutes the inner shaft of the rod 607, is screwed in a rear end portion of the connection member 671, whereby the connection member 671 is electrically connected to the inner shaft 675 of the rod 607.

The rod 607 includes the inner metal shaft 675 and an outer metal pipe 676 containing the former. An insulation tube 677 made of a resin is fitted on the outer periphery of the inner shaft 675. Since the insulation tube 677 is thus interposed between the inner shaft 675 and the outer pipe 676, the shaft and pipe are electrically insulated from each other.

A cylindrical distal end cover 678 made of a metal, whose front end portion is formed into the left and right support arm portions 620, is fixedly fitted on a distal end portion of the outer pipe 676. The distal end cover 678 is electrically connected to the outer pipe 676.

As shown in FIGS. 48B, 48F and 48G, the outer periphery of the connection member 671 is covered with an insulation cover 679. The insulation cover 679 electrically disconnects the connection member 671 from the distal end cover 678 and the support arm portions 620. An electrically insulated pin 680 is buried in the connection member 671 covered with the insulation cover 679.

As described above, the inner shaft 675 and the outer pipe 676 of the rod 697 are electrically insulated from each other. Further, the inner shaft 675 is electrically connected to the lower jaw 608b, while the outer pipe 676 is electrically connected to the upper jaw 608a.

To secure this electrical relationship, the distal end of the inner shaft 675 of the rod 607 is connected to the rear end portion of the connection member 671, which is, directly or via the pin 672, connected to the lower jaw 608b. Further, the connection member 671 and the pin 672 are electrically disconnected by the insulation cover 681 from the support arm portions 620 of the distal end cover 678. The insulation cover 681 is attached to the inner surfaces of the support arm portions 620. The insulation cover 681 extends up to the upper and lower edges of the support arm portions 620. In particular, as shown in FIG. 48C, lower portions of the cover 681 are curved so that they reach the outer surfaces of the support arm portions 620, thereby maximizing the length of insulation. As a result, the electrical insulation effect of the insulation cover 681 is increased. A protection tube 685 is fitted on the pivot pin 667. The protection tube 685 bridges all the pivot pin bearings.

The inner shaft 675 of the rod 607 is electrically connected to the lower jaw 608b via the connection member 671 and the pivot pin 672, or via only the connection member 671. The outer pipe 676 is electrically connected to the upper jaw 608a via the distal end cover 678, the pair of support arm portions 620 and the pivot pin 667. Both the electrical conduction paths are electrically isolated from each other by an insulation member such as the insulation tube 677.

Figures 47A, 47B, 47C:
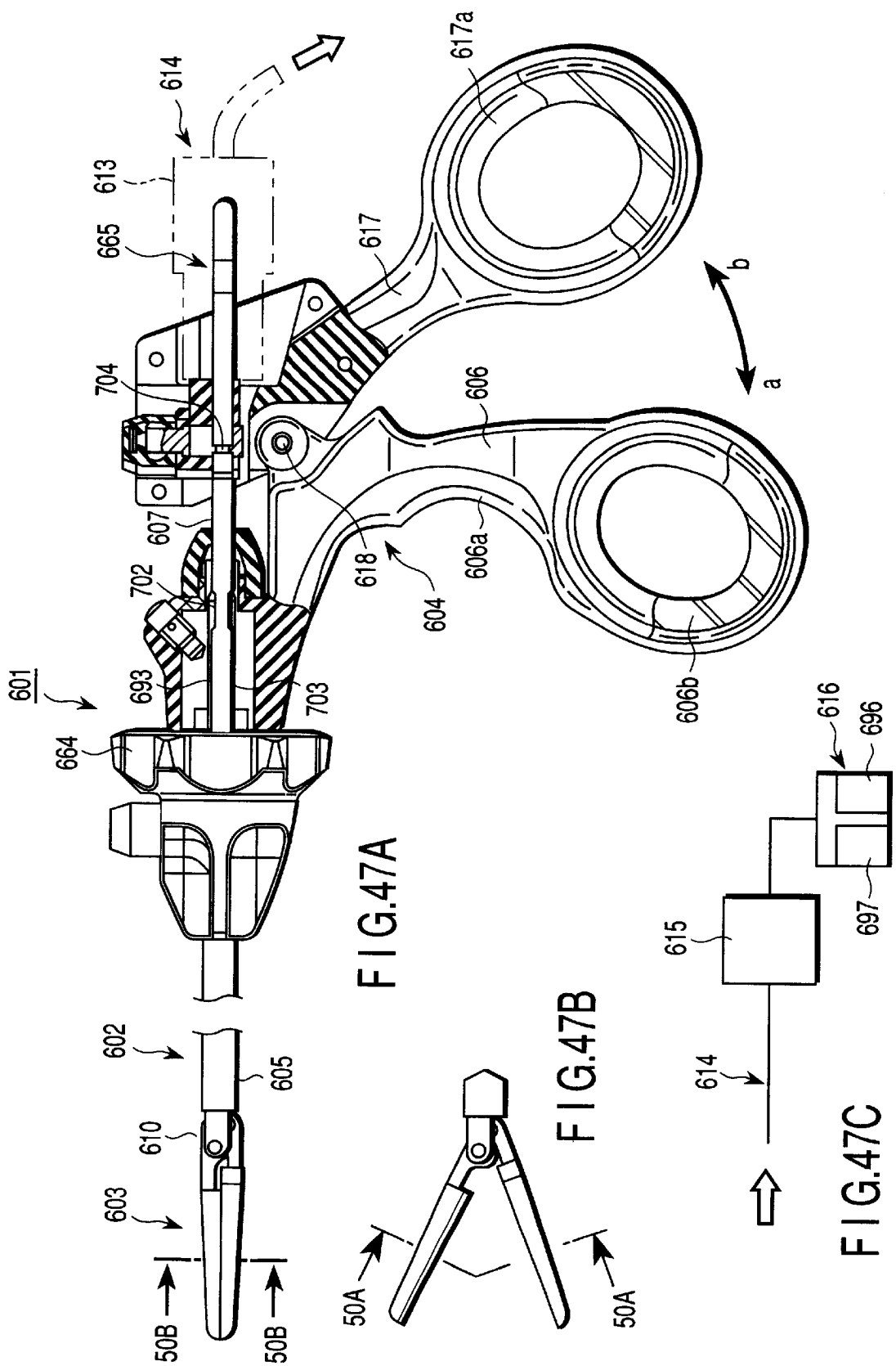
FIG. 47A is a view illustrating a high-frequency treatment tool according to a 24th embodiment of the present invention.
FIG. 47B is a view illustrating a treatment portion of the high-frequency treatment tool according to the 24th embodiment of the present invention.
FIG. 47C is a view illustrating a foot switch employed in the high-frequency treatment tool according to the 24th embodiment of the present invention.

As shown in FIG. 47A, the rod 607 of the treatment tool unit 665 extends through the insertion portion 602 and the operation portion 604, and has its rear end protruded from the rear end of the operation portion 604. As shown in FIG.

49A, the inner shaft 675 of the rod 607 is fixedly screwed in a first connection terminal member 691 as a rearmost member. The outer pipe 676 is connected to a second connection terminal member 692 via a conductive engagement tube 693. The insulation tube 677 and an electrically insulated tube 694 are interposed between the first and second connection terminal members 691 and 692.

The outer pipe 676 is electrically connected to the second connection terminal member 692 via the engagement tube 693, while the inner shaft 675 is electrically connected to the first connection terminal member 691 as the rearmost member. The insulation tube 694 interposed between the first and second connection terminal members 691 and 692 electrically disconnects the inner shaft 675 from the outer pipe 676. The distal end of the insulation tube 677 fitted on the outer periphery of the inner shaft 675 extends up to the electrically insulated tube 694 and is connected to it.

When, as shown in FIG. 47A, the connector-receiving portion 613 of the cable 614 extending from the high-frequency cautery power supply unit 615 is connected to the first and second connection terminal members 691 and 692 of the rod 607, the supply of power is enabled. The high-frequency cautery power supply unit 615 is provided with a foot switch 616 having an incision pedal 696 and a coagulation pedal 697.

Figure 49A:
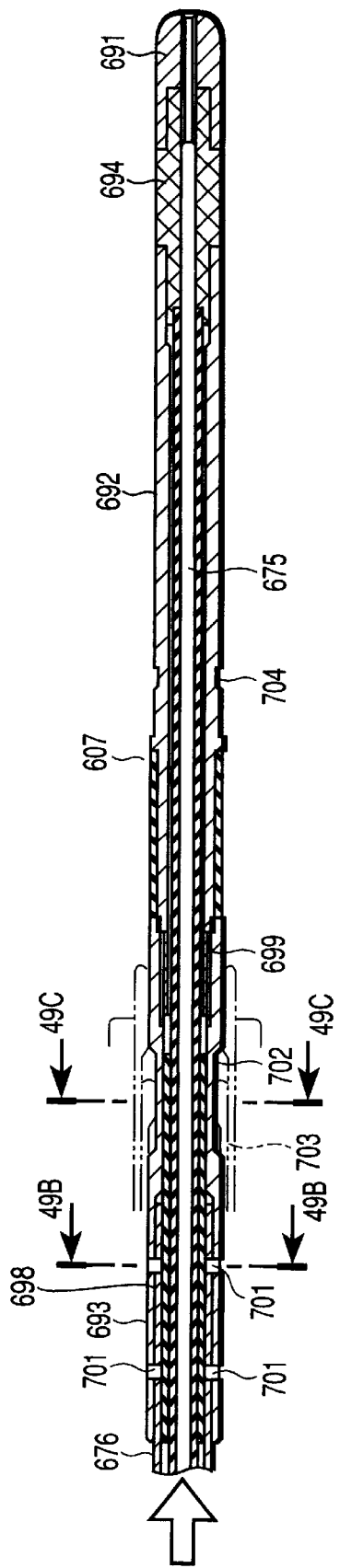
FIG. 49A is a longitudinal sectional view illustrating a proximal end portion of a rod incorporated in the high-frequency treatment tool shown in FIG. 47A.
Figure 49C:
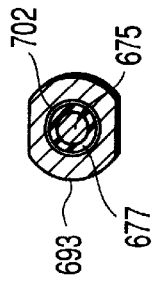
FIG. 49C is a sectional view taken along line 49C—49C in FIG. 49A.

As shown in FIG. 49C, the engagement tube 693 is formed of a pipe member larger in diameter than the outer pipe 676 and sufficiently thicker than it. The outer pipe 676 is coupled to the engagement tube 693 by fitting a rear end portion of the outer pipe 676 into a front end portion 698 of the engagement tube 693. A male screw portion 669 engaged with the rear end portion of the engagement tube 693 is provided as a front end portion of the second connection terminal member 692.

Figure 49B:
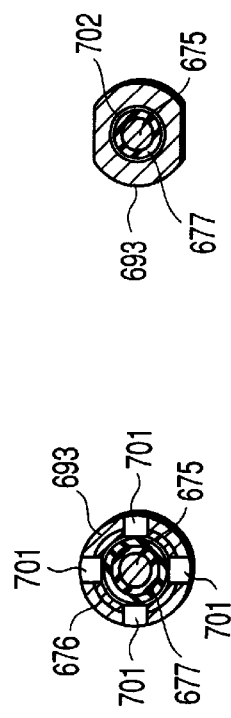
FIG. 49B is a sectional view taken along line 49B—49B in FIG. 49A.

As shown in FIG. 49B, a plurality of pins 701 are buried, by firm fitting, in the front end portion 698 of the engagement tube 693, in which the rear end portion of the outer pipe 676 is fitted, thereby firmly coupling the outer pipe 676 to the engagement tube 693. A plurality of flat engagement portions 702 are formed at the outer periphery of a middle portion of the engagement tube 693 by cutting off peripheral portions of the middle portion. When the treatment tool unit 665 is connected to the insertion portion 602, the engagement portions 702 are engaged with engagement portions 703 provided on the insertion portion 602. As a result, the treatment tool unit 665 is engaged with the insertion portion 602 so that they can rotate together. Furthermore, a groove 704 is formed in a middle portion of the front end portion of the second connection terminal member 692, and engaged with the trigger 617. By virtue of the groove 704, the trigger 617 can axially move the rod 607.

When the rod 607 has axially shifted, the jaws 608a and 608b are pivoted on the link mechanism 610, thereby opening and closing the distal end portions of the jaws. In other words, the treatment portion 603 assumes the closed state shown in FIG. 47A and the open state shown in FIG. 47B.

Figure 50A:
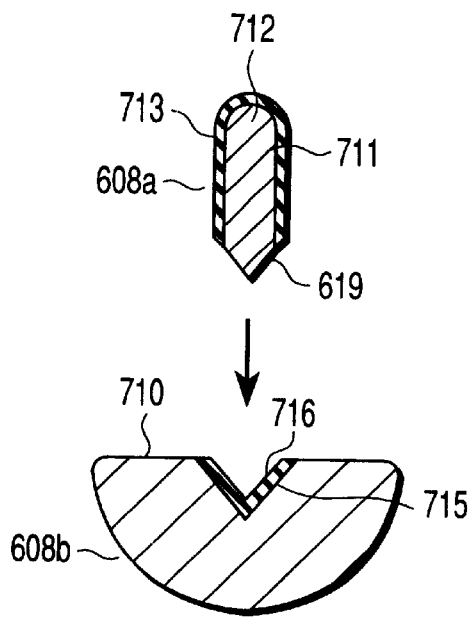
FIG. 50A is a transverse sectional view illustrating the open state of a treatment portion incorporated in the high-frequency treatment tool shown in FIG. 47A.
Figure 50B:
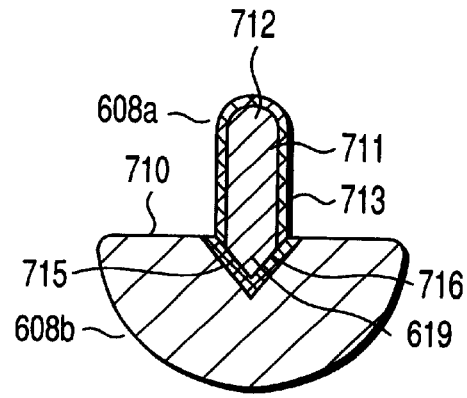
FIG. 50B is a transverse sectional view illustrating the closed state of the treatment portion incorporated in the high-frequency treatment tool shown taken along line 50B—50B in FIG. 47A.

A description will be given of the jaws 608a and 608b that constitute the treatment portion 603. As shown in FIGS. 50A and 50B, the upper and lower jaws 608a and 608b have different transverse cross sections. The lower jaw 608b has a flat and wide gripping surface 710 and a substantially-semicircular and laterally-wide transverse cross section.

On the other hand, the upper jaw 608a has a transverse cross section of a narrow width, and includes a blade member 711 in the form of a thin plate having a thin thickness (narrow width) in the direction perpendicular to the pivoting direction of the jaw when gripped. The gripping-side end of the blade member 711 is formed into an incision portion 619 as a wedge-shaped cutting edge. The blade member 711 also has an arcuate back portion 712. Further, the blade member 711 has a transverse cross section of a narrow width substantially constant from the back portion to a proximal end of the incision portion 619 as the cutting edge. The incision portion 619 is tapered from its proximal end to its distal end. This cross section of the blade member is similar to that of the incision area portion of the upper jaw 608a of the first embodiment, which is provided with the incision portion 619.

Figure 53:
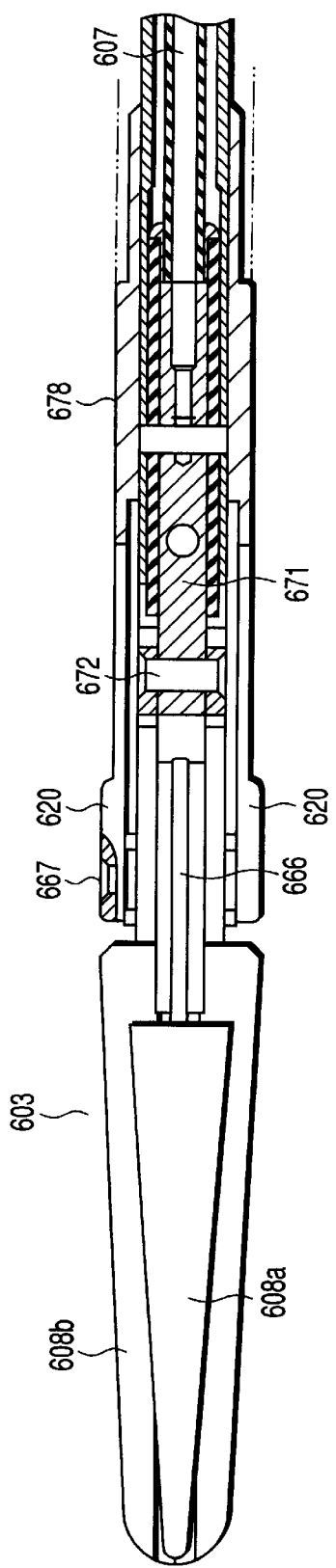
FIG. 53 is a longitudinal sectional view illustrating a modification of the high-frequency treatment tool according to the 24th embodiment of the present invention.

Further, as shown in FIG. 48B, the blade member 711 of the upper jaw 608a, which is provided with the incision portion 619, has a narrow width. The entire upper jaw 608a has the same shape as this. However, the blade member 711 of the upper jaw 608a may be formed gradually thicker (wider in width) towards its proximal end, as shown in FIG. 53.

As shown in FIGS. 50A and 50B, an insulation member 713 is provided on the outer surface of the upper jaw 608a except for on the incision portion 619. The insulation member 713 is formed by, for example, alumina coating. Although, in this embodiment, the insulation member 713 is not provided on the lower jaw 608b, it may be provided on the outer surface of the lower jaw except for on a gripping surface 710 thereof, as in the 22nd embodiment.

A groove 715 to be engaged with the incision portion 619 of the upper jaw 608a is formed in that portion of the gripping surface 710 of the lower jaw 608b, which is opposed to the incision portion 619. The groove 715 has a cross section of a substantially inverted triangle. An insulation layer 716 is provided on the inner surface of the groove 715 by, for example, alumina coating.

Figure 51A:
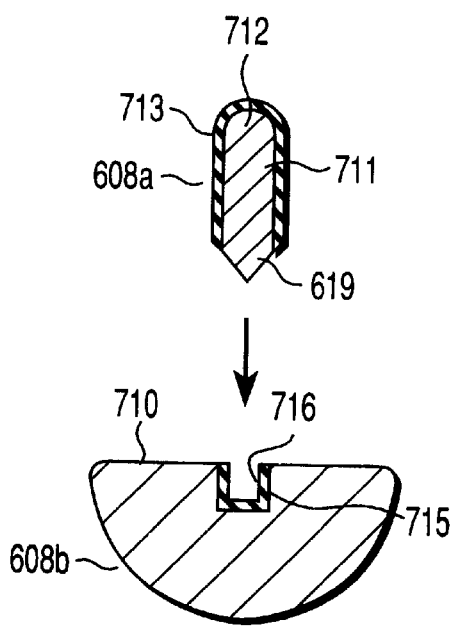
FIG. 51A is a transverse sectional view illustrating the open state of a treatment portion incorporated in a modification of the high-frequency treatment tool shown taken along line 50A—50A in FIG. 47A.
Figure 51B:
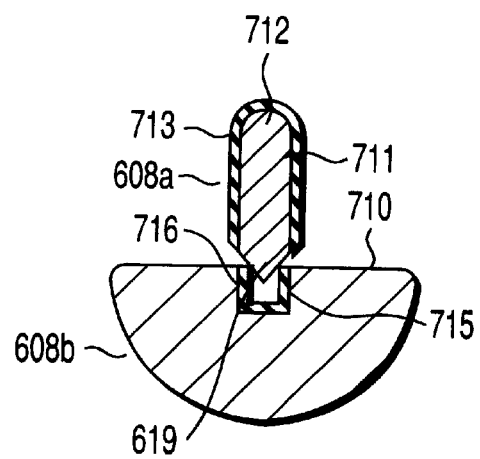
FIG. 51B is a transverse sectional view illustrating the closed state of the treatment portion incorporated in the modification of the high-frequency treatment tool shown in FIG. 47A.

When the incision portion 619 of the upper jaw 608a is engaged with the groove 715 of the lower jaw 608b, it is actually in contact with the insulation layer 716 and not with the metal body of the lower jaw 608b. Accordingly, even when the incision portion 619 is engaged with the groove 715, the upper and lower jaws 608a and 608b do not short-circuit. The shape of the cross section of the groove 715 is not limited to the inverted triangle, but may be a rectangle as shown in FIGS. 51A and 51B.

Further, as shown in FIG. 48B, the blade member 711 of the upper jaw 608a has the same thickness (width) over the entire length thereof, while the gripping surface of the lower jaw 608b is thinner (narrower in width) towards its tip. Both the upper and lower jaws 608a and 608b are formed linearly in the longitudinal direction of the insertion portion 602.

Alternatively, both the jaws 608a and 608b may be curved as shown in FIG. 52A. FIG. 52B is a longitudinal sectional view illustrating the lower jaw 608b, and FIG. 52C is a transverse sectional view taken along line C—C in FIG. 52B.

FIG. 53 is a plan view illustrating the upper jaw 608a, FIG. 52E is a side view illustrating the upper jaw 608a, and FIG. 52F is a view taken along line F—F in FIG. 52D. As shown in FIG. 52C, in this embodiment, the insulation layer 716 provided on the inner surface of the groove 715 extends to the flat gripping surface 710 (but not on the entire flat surface).

When incising tissue by the high-frequency treatment tool 601 of this embodiment, the tissue is held between the jaws 608a and 608b of the treatment held between the jaws 608a and 608b of the treatment portion 603, and a high frequency current is flowed therebetween. The high frequency current flowing between the jaws 608*a* and 608*b* concentrates on the incision portion 619, thereby incising the tissue.

Since the blade portion of the jaw 608*a* in the area provided with the incision portion 619 has a narrow width, the phenomenon is avoided in which the blade portion may grip target tissue as well as the tissue surrounding the target tissue when the incision portion 619 incises the target tissue. No tissue is brought into contact with the blade portion of the jaw 608*a* other than at the sharp incision portion 619, and the left and right portions of the tissue incised by the incision portion 619 are laterally parted by the jaw 608*a* in a smooth manner. Accordingly, the advance of the incision portion 619 of the jaw 608*a* is not interrupted. As a result, the incision portion 619 effectively functions as a sharp blade, and a high frequency current concentrates on its cutting edge, thereby executing efficient incision. Since, thus, only the incision portion 619 of the jaw 608*a* can smoothly cut into only the tissue to be incised or coagulated, only the target tissue can be incised or coagulated.

In the high-frequency treatment tools according to the 22nd to 24th embodiments, the coagulation portion having wide gripping surfaces is provided at the proximal end side of two gripping members, and at least one of the gripping members has a projecting incision portion (formed of an incision electrode) provided at their distal end side and extending in the axial direction of the insertion portion. This very simple structure, however, enables easy execution of treatments such as coagulation, incision, gripping and peeling of vital tissue. Moreover, since the portion of the blade member, which is provided with the projecting incision portion, has a transverse cross section of a narrow width in the direction of incision, the incision portion can cut into target tissue smoothly while incising the tissue using a high frequency current. As a result, only the to-be-incised tissue can be efficiently incised using the high frequency current.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bipolar high-frequency treatment tool comprising:
   (i) an elongated member;
   (ii) a pair of jaws provided adjacent to a distal portion of the elongated member so as to grip vital tissue, wherein the pair of jaws are movable relative to each other between a closed position and an open position;
   (iii) a handle assembly provided adjacent to a proximal portion of the elongated member, wherein the handle assembly is coupled operatively with at least one of the jaws, and the pair of jaws are movable relative to each other between the closed position and the open position so as to grip the vital tissue between the jaws in accordance with an operation of the handle assembly;
   wherein one of the jaws comprises a first conductive member, and the first conductive member includes a first electrode portion that can be brought into contact with vital tissue when the jaws are operated to grip the vital tissue between the jaws, and the first electrode portion defines a first area;
   wherein the other of the jaws comprises a second conductive member, and the second conductive member comprises a second electrode portion that can be brought into contact with vital tissue when the jaws are operated to grip the vital tissue between the jaws, and the second electrode portion defines a second area which is made smaller than the first area such that a treatment high-frequency current for coagulation/incision of the vital tissue is concentrated to the second electrode portion when a bipolar high-frequency treatment is carried out; and
   (iv) a power supply unit electrically connected to the first electrode portion and the second electrode portion such that the treatment high-frequency current is allowed to flow between the first electrode portion and the second electrode portion, wherein the power supply unit is operable in a constant power output mode in which a constant power is maintained even if an impedance is increased such that the treatment high-frequency current for the coagulation/incision of the vital tissue is allowed to flow between the first and second electrode portions.

2. The high-frequency treatment tool according to claim 1, wherein the second electrode portion comprises a projection formed of a conductive material member projecting from one of the jaws toward the other jaw.

3. The high-frequency treatment tool according to claim 2, wherein the second electrode portion is elongated in a longitudinal direction of the elongated member.

4. The high-frequency treatment tool according to claim 1, wherein the second electrode portion comprises a blade-shaped member having a transverse cross section that is elongated in a direction of incision.

5. The high-frequency treatment tool according to claim 1, wherein the one of the jaws has a gripping surface provided with a groove to be engaged with a distal end of the second electrode portion when the jaws are closed.

6. The high-frequency treatment tool according to claim 1, wherein the one of the jaws has a gripping surface in an area other than an area provided with the first electrode portion, and the gripping surface is used for gripping the vital tissue.

7. The high-frequency treatment tool according to claim 1, further comprising a short circuit preventing unit for determining closure termination positions of the jaws to prevent the first and second electrode portions from coming into contact with each other when the jaws are closed.

8. The high-frequency treatment tool according to claim 7, wherein the short circuit preventing unit includes an electrically insulating member provided on the one of the jaws on which the first electrode portion is formed, wherein the second electrode portion is struck against the electrically insulating member, thereby determining the closure termination positions of the jaws and preventing the first and second electrode portions from coming into contact with each other.

9. The high-frequency treatment tool according to claim 1, wherein outer surfaces of the jaws except the first and second electrode portions are electrically insulated.

10. The high-frequency treatment tool according to claim 1, wherein the second electrode portion has a sharp distal end that constitutes the second area.

11. The high-frequency treatment tool according to claim 1, wherein the second electrode portion comprises a projection projecting from the other jaw toward the one jaw, the projection comprises a sharp distal end having a substantially V-shaped transverse cross section, and the sharp distal end constituting the second area.

12. The high-frequency treatment tool according to claim 1, wherein the jaws each have a width that gradually reduces toward a distal end thereof.

13. The high-frequency treatment tool according to claim 12, wherein the jaws each have a height that gradually reduces toward a distal end thereof.

14. The high-frequency treatment tool according to claim 1, wherein the jaws each have a height that gradually reduces toward a distal end thereof.

15. The high-frequency treatment tool according to claim 1, wherein said one of the jaws has a gripping surface for gripping vital tissue.

16. The high-frequency treatment tool according to claim 15, wherein the gripping surface includes two surface parts, between which the second electrode portion is provided.

17. The high-frequency treatment tool according to claim 15, wherein a treatment portion including the first and second electrode portions is provided over substantially an entire length of the jaws.

18. The high-frequency treatment tool according to claim 1, wherein said other of the jaws includes a blade member formed from a conductive material, and the blade member has a cross section elongated in a direction in which said other of the jaws is opened and closed.

19. A bipolar high-frequency treatment tool comprising:
a first jaw including a first grip member for gripping a vital tissue, wherein the first grip member is made of a conductive material and has a first contact portion that is brought into contact with the vital tissue when the vital tissue is gripped;
a second jaw including a second grip member for gripping the vital tissue between the first grip member and the second grip member, wherein the second grip member is made of a conductive material and has a second contact portion that is brought into contact with the vital tissue when the vital tissue is gripped with the first grip member, wherein the second contact portion is larger than the first contact portion such that a treatment high-frequency current for coagulation/incision of the vital tissue is concentrated to the first electrode portion when a bipolar high-frequency treatment is carried out, wherein the second contact portion has an insulation member at a position which is located to face the first contact portion when the vital tissue is gripped between the first grip member and the second grip member, and wherein the insulation member insulates the first contact portion and the second contact portion from each other;
a power source, which is electrically connected to the first grip member and the second grip member, for providing a high-frequency current to be passed to the vital tissue, wherein the power source supplies currents to the first grip member and the second grip member so that the first grip member and the second grip member function as bipolar electrodes, and wherein the power source is operable in a constant power output mode in which a power is maintained even if an impedance is increased such that the treatment high-frequency current for the coagulation/incision of the vital tissue is allowed to flow between the first and second electrode portions;
a support member for supporting the first jaw and the second jaw to be insulated from each other such that the first jaw and the second jaw are movable relative to each other to be openable/closable between an open position and closed position, wherein the first contact portion is brought into contact with the insulation member when the first jaw and the second jaw are set at the closed position; and
an operation unit having a handle for moving the first jaw and the second jaw relative to each other to open/close the jaws.

20. The high-frequency treatment tool according to claim 19, wherein an insulation layer covers the first jaw except at least the first contact portion.

21. The high-frequency treatment tool according to claim 20, wherein the jaws each have a height that gradually reduces toward a distal end thereof.

22. The high-frequency treatment tool according to claim 19, wherein at least one of the first and second jaws is curved.

23. The high-frequency treatment tool according to claim 19, wherein the handle of the operation unit is connected to a rod that is movable in accordance with manipulation of the handle to open and close the first and second jaws.

24. The high-frequency treatment tool according to claim 19, wherein the support member comprises a first jaw rotation axis and a second jaw rotation axis via which the first and second jaws are supported.

25. The high-frequency treatment tool according to claim 19, wherein the support member comprises a rod and support arms via which the first and second jaws are supported.

26. The high-frequency treatment tool according to claim 19, wherein the first grip member comprises a projection projecting from the first jaw toward the second jaw.

27. The high-frequency treatment tool according to claim 26, wherein the first grip member is elongated in a longitudinal direction of the first jaw.

28. The high-frequency treatment tool according to claim 19, wherein the first grip member comprises a blade-shaped member having a transverse cross section that is elongated in a direction of incision.

29. The high-frequency treatment tool according to claim 19, wherein the second grip member is divided into a plurality of electrode components, and each of the electrode components is provided on the one of the jaws.

30. The high-frequency treatment tool according to claim 19, wherein outer surfaces of the jaws other than the first and second grip members are electrically insulated.

31. The high-frequency treatment tool according to claim 19, wherein the first grip member comprises a projection projecting from the first jaw toward the second jaw, and the projection includes a sharp distal end having a substantially V-shaped transverse cross section, and the sharp distal end constitutes the first contact portion.

32. The high-frequency treatment tool according to claim 19, wherein the jaws each have a width that gradually reduces toward a distal end thereof.

33. The high-frequency treatment tool according to claim 19, wherein the jaws each have a height that gradually reduces toward a distal end thereof.

34. The high-frequency treatment tool according to claim 19, wherein each of the first and second grip members comprises a blade member formed from a conductive material, and the blade members have a cross section that is elongated in a direction in which the jaws are opened and closed.

* * * * *